(12) United States Patent
Koduri et al.

(10) Patent No.: US 6,800,457 B2
(45) Date of Patent: *Oct. 5, 2004

(54) EXPRESSION VECTORS CONTAINING HOT SPOT FOR INCREASED RECOMBINANT PROTEIN EXPRESSION IN TRANSFECTED CELLS

(75) Inventors: Kanaka Raju Koduri, White Plains, NY (US); John T. Miller, Syracuse, NY (US); Pallaiah Thammana, Manlius, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/320,176

(22) Filed: Dec. 16, 2002

(65) Prior Publication Data

US 2003/0138908 A1 Jul. 24, 2003

Related U.S. Application Data

(63) Continuation-in-part of application No. 09/386,816, filed on Aug. 31, 1999, now Pat. No. 6,521,419.
(60) Provisional application No. 60/101,292, filed on Sep. 22, 1998.

(51) Int. Cl.[7] .................................................. C12P 21/02
(52) U.S. Cl. ..................... 435/69.1; 435/69.6; 435/358; 435/320.1
(58) Field of Search ............................... 435/69.6, 69.1, 435/358, 320.1; 536/24.2

(56) References Cited

U.S. PATENT DOCUMENTS

| | | |
|---|---|---|
| 5,747,034 A | 5/1998 | de Boer et al. |
| 5,773,253 A | 6/1998 | Linsley et al. |
| 5,844,095 A | 12/1998 | Linsley et al. |
| 6,521,419 B1 * | 2/2003 | Koduri et al. ............. 435/69.1 |

FOREIGN PATENT DOCUMENTS

| | | |
|---|---|---|
| WO | WO 93/00431 | 1/1993 |
| WO | WO 95/17516 | 6/1995 |
| WO | WO 97/25420 | 7/1997 |

OTHER PUBLICATIONS

Dillon et al., Trends In Genet., vol. 9, No. 4, pp. 134–137 (1993).
Grosveld et al., Cell, vol. 51, pp. 975–985 (1987).
Phi–Van et al., Mol.Cell, Biol. vol. 10, No. 5, pp. 2302–2307 (1990).
Gasser et al., Trends In Genet. vol. 3, pp. 16–22 (1987).
Kellum et al., Cell, vol. 64, pp. 941–951 (1991).
Bode et al., Science, vol. 255, pp. 195–197 (1992).
Little et al., Nature, vol. 366, pp. 204–205 (1993).
Sohn et al., Journal of Bacteriology, vol. 178, No. 15, pp. 4420–4428 (1996).
Caddle et al., J. Mol. Biol., vol. 211, pp. 19–33 (1990).
Buhrmester et al., Biochemistry, vol. 34, pp. 4108–4117 (1995).
Orr–Weaver et al., Proc. Natl. Acad. Sci. USA, vol. 78, No. 10, pp. 6354–6358 (1981).
Symington et al., The Journal of Immunology, vol. 150, No. 4, pp. 1286–1295 (1993).

* cited by examiner

*Primary Examiner*—James Ketter
(74) *Attorney, Agent, or Firm*—Briana C. Buchholz; Christopher A. Klein

(57) ABSTRACT

A specific locus (hot spot) for recombinant gene expression has been identified in the genome of Chinese hamster ovary cells. A DNA vector containing the hot spot causes high levels of recombinant gene expression following transfection and stable integration. The selection and cloning of the specific locus and the expression of recombinant genes is disclosed, as are the DNA vectors and the host cells.

27 Claims, 10 Drawing Sheets

- 5.0 kb genomic sequence at 5' end of CTLA4-Ig gene

- Genomic Sequence split between 5' and 3' end of CTLA4-Ig gene

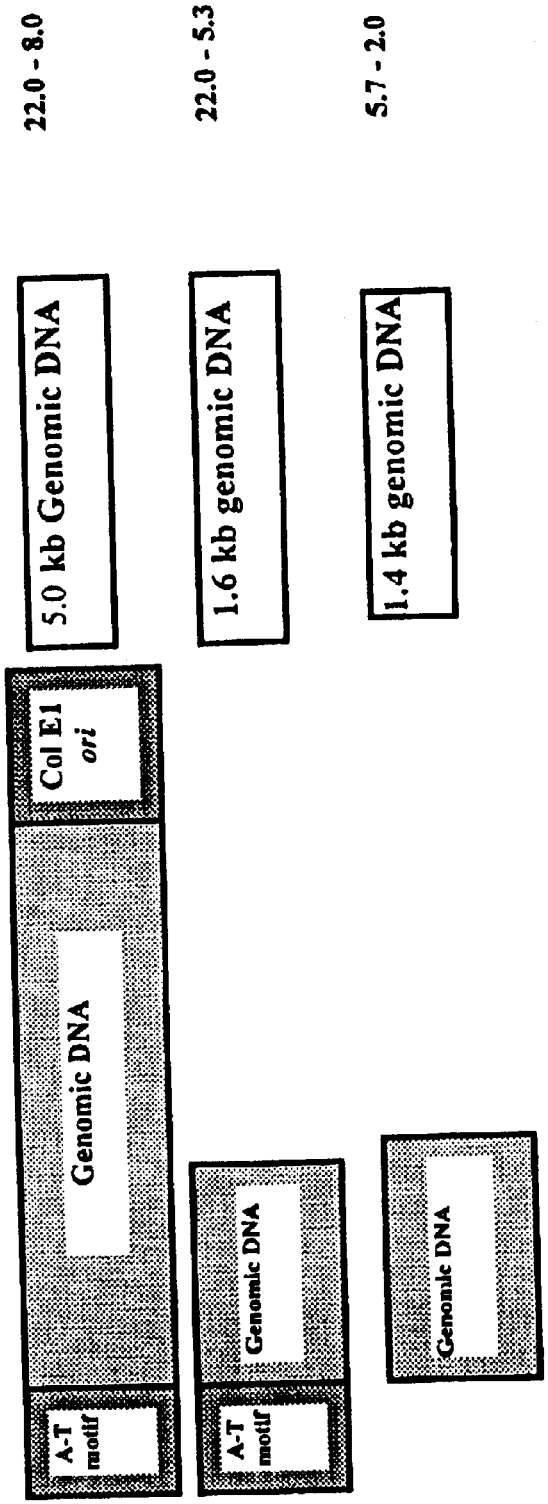

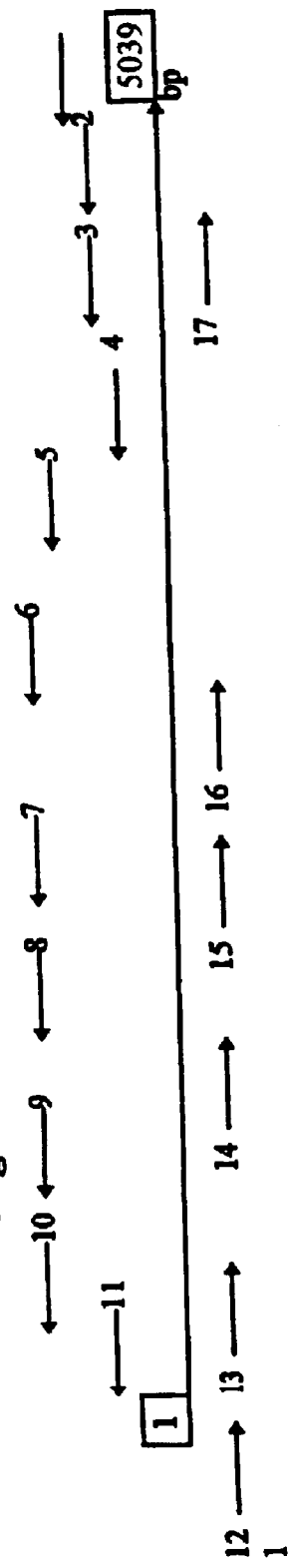

FIG. 9

Oligonucleotides used to obtain the HIRPE sequence

1. CGTGTACGGGTGGGAGGTCTA (SEQ ID NO:15)   2. AATTGCTACGTGGTGGTGTC (SEQ ID NO:16)
3. GGCTGACTCTTCACTGGTAG (SEQ ID NO:17)   4. ACAGAGCCTACTCCATCATC (SEQ ID NO:18)
5. GTCTTCTTGGCCTGTC (SEQ ID NO:19)   6. GTGCTTATTTCATGTCTGGC (SEQ ID NO:20)
7. TGACGGATTGCTTCAG (SEQ ID NO:21)   8. CATCTCGCACCTCTATCAGT (SEQ ID NO:22)
9. GGCCTCAGAGTCCATACTGT (SEQ ID NO:23) 10. TCTCCACAGCGACTGCACTA (SEQ ID NO:24)
11. GACTGTAGCTCAGTGGTAGA (SEQ ID NO:25) 12. TTCGAGGGAGCACGCGACA (SEQ ID NO:26)
13. ATCCTTGGCCACTGCCTAT (SEQ ID NO:27) 14. ATGTCTGTGTTCCTGTTAGTG (SEQ ID NO:28)
15. CCGGTCACATTGTGTTCA (SEQ ID NO:29) 16. CATCTCGCACCTCTATCAGT (SEQ ID NO:30)
17. GGCATACATGTGGACCATTC (SEQ ID NO:31)

US 6,800,457 B2

SEQUENCE LISTING

<160> NUMBER OF SEQ ID NOS: 31

<210> SEQ ID NO 1
<211> LENGTH: 5039
<212> TYPE: DNA
<213> ORGANISM: Cricetulus griseus

<400> SEQUENCE: 1

```
taggctagcc tgcccacaag cttcctggct cctcctaaca tctcccttta aatcactggg      60
ctcaccaaca ttcctgctgc agtgtcaggt ttgttcctga ctttagggat tcaaactcag     120
gtcctcacac ttgtgttgca aaagcttact cagagagtca tctgctcaca cccggctgtt     180
tgtgttttga gacagggtct ccctatgtat ctcaggctga cctccaactg actcccttcc     240
tcctaactgc ctccctagtg ctaggatccc aggcctttct tcccatgatt ctgggaaagg     300
caagactagg gacaactccc tggtatactg agggctcctg cagggaccct tgcatcccat     360
ccttggccag tggcctatag ggactccctg tgatccctgc tttctagcat tgccctgctc     420
cactcagttc ttgttacttt aatcacttcc aacattaagt ttttgaaaaa ttgcagtttc     480
taccctgaga acatacacaa atgactcatg ggcgagaaga ctctcagtgc ccacatcatt     540
gcagagattc agatcaaaac tccagtgagt catcacttca accccctggg aagagcacat     600
caaaaacaat tcttttcttt tcttctcttt tcttttcttt tctttctttt tctgacaaca     660
ctggggattg agtctaaggc ctcatgcacc ttaggcaagc gctctaccac tgagctacag     720
tcctaacttt ttttttttctt tttaagaaca ataaaaaaca aaaacaaaat ataaaacaag     780
ggaaacatgg aggcacatgc tggtaatccc aacactacag aggcaaagac agaggcagga     840
aggacataat aaattccaga ccagctggtg ttagaatgag accctgtctc agaaagaaag     900
aaaaaaaaga aagaaagaaa gaaaggaaga aagaaagaaa gagggaggga ggagggagaa     960
agagaggaat gggcaaggat gtagagagac gagaaacttt gtgcactatc atgaaagcaa    1020
aatagtgcag tcgctgtgga gaatggtatg gtaatgctgg aaagaaggct catcgaggaa    1080
atgaccttgc aaccaaaccc gaagacctga gtttgatccc tgatacctac atggtagaag    1140
aactaactct atcaagtagt cctttgactt ccaaatgtat gctgtggcac atacagtcct    1200
cttcccccaa taaataatgt aattaaaaaa agaaaagggg ctggagagat ggctcagtgg    1260
ttaagagcat tggctcttaa tccagagaac ccgggttcaa ttcccagcac ccacatagca    1320
gcttacaact gcctccaggg ggtccaacac cctcacacag acatacacac agataaacag    1380
caatgtacat aaaataaata aattattttt aacaacaaca aaaaaaatg aaaagaaaag    1440 aaggctgggc agtggtggca caccacatac ctttagtctt tgtactcagg agtcagagac    1500
```

```
cggcagatct ctgtgagttt gaggccagcc tggtctacaa agcaagttcc agaacatcca   1560
gggctgttac acagagaaac ctcaaaataa aataaaataa aataaaataa aatggaagaa   1620
acaaacaaag aaagaaagaa agaagaaaag aaaagtgaaa aagagcatga tagttcttca   1680
gaaagttaag cgttgctact gatggtggcc tgaagtcctg tcttcaatac tccacaataa   1740
gtaatagtgt gcaaacaagt acataatcca gctaagcact aaattaccca tgatcttcct   1800
ctttggtgta tacctcaaag agttgacagg cagccttatt agagtgacat tgtctttaaa   1860
cccagcatga ccatcctgat gaactgctgt gatgcccagg gaagacaggg taacctcgaa   1920
gtccaagtac ttccttaaga ccatttaact tctggatgat tattaaaaat gcttcattgt   1980
aggagcagac agtatggact ctgaggccat cagcagattg catatccctt caagggaaga   2040
ctgtggggct gatgggcaag aaaccaaaat agctaacaag agctatttaa ggcaggaaga   2100
gtccatgttg gtttgcagtt caagggtaca gtccatcacg gtgaagaaga caagatggca   2160
gaagcatggg gcaaccggtc acattgtgtt caccaacagg aaacagaaaa caacaaatgc   2220
cgtgctgggc tcactttctc cttttttcct tttcattcag cttggaactg ctacccgtga   2280
gatgatgcca cccatgttca gggtagatct tccctttttt tgttgagctt ctctagaaat   2340
accctcaaag acacatacag tagtatgcct cccagaggac tctaattgca atgtagttga   2400
caaggaagtt taaccatcat agccggcaaa cctagggttg atacctttaa tatagattcc   2460
tttcggtagt ctgagtatgc ctagtctaat gcttgagtct tcgaaaagaa ctccagctgg   2520
aggctgagag attcattggt gcacgttgca gtttgcatgg ggagaggctg ctgtctgtgg   2580
ctgaagggag cagtgtgcag agtatgagga tgaataggag aagagctagg tgcaaagtcc   2640
accgtccact tgtcacgggg cccctggatg accaccatca aggaaatgga gaccaatacc   2700
tgaaagggtt tgagtatggc caatgaggca gaagaaattg agagtgagtc aaccctagag   2760
gaagatctac aactctgctg accccatgat gttgacctta tgaagctaaa acataataaa   2820
tggacttcca ctgatagagg tgcaagatga acaagcctat ctcattcgtc agtcactgaa   2880
cttgggatga tctgttaggg cagcaacaga aaactaatat aaatatatat gtatatgata   2940
tttattggtt tttcagtact ttcctagtga gagtcattgc tatgcagata ttgcacgatg   3000
ctatttatca ctttccactt acccagctga agcaatccgt cactatctga gagcctctct   3060
gcagttcaga tttgagtgtc acaggcattg tttctgaggc tctctgggaa acgtactcct   3120
tctctacagg agcctggcgt ctggctggag aaagactgag tgcctgaggg ttgtttcaga   3180
ggcaccaatc aatactcacc attaggacaa caactccacg catcactaaa ctttgacctc   3240
cgtgctccag agaggtccca agatgccaat tgatgcacag gccatataca tagtccatga   3300
atgcaatgcc ttcatagact cctgtgaatt aaatcataga gactttagca atggcaacat   3360
aatgttgtta atgtactagc aagcctggaa tgtgtacaga gaatgcctgg attaaagctg   3420
tgatggtatt tgtgccttta agaaaggctt gtgtctttaa aaaggtcttg aggataaatt   3480
ctgcattcag aatgttggct agctgtcact gtcctctata tgactgggtg gtgctggcat   3540
aagatgtctt gtaagccaga catgaaataa gcacttgtgt gtagccccaa gacccaacaa   3600
caagcttgag tacacaccct tcctagaaat cagaagacag gccaagaaga cctttaagtg   3660
tgtttctctt ttatgtgaaa ctttgtggat tttatttccc cagaaatgcg ttttgggggg   3720
acttcttcat tatggtctat tgtcacataa attgtgctct tcacagaaaa gggtgatgaa   3780
accctgttcc ttgactgggt tgagtgggat ccactgccaa acagctgtct gggctaaaac   3840
```

-continued

```
agaatagctg atttggaaag acttaaaagg gtaatcattt tgatgttggt gggagttcgt    3900
atctgaatgc catgttatag cttcttatat ccaatcagaa tggtccacat gtatgccctg    3960
tgtgccaaca gaggtctcca gtgcctccta taagaagggc tagcaggaga gaagacatga    4020
agtccattga agaaaaagtt acagacttca aaagcaccaa aaatcactgg gaaccaaagc    4080
aagtttccca ctatccccgc cccccccctt gctggtttct tctgaaatgt tatgcctctt    4140
gataattggc ctgcccaagg ttgcaacctt catgtgcctt gggtccattt cacttctagc    4200
tctttaagta tataaataaa tagataatta gatgatggag taggctctgt gggctttact    4260
tcattcatct ggctcctgaa cttgaatcca ggcccatttg aaatcccagg gaaggttttg    4320
gctgggtgtg gggcatagc tgtgttccag ttggctgact cttcacctgg tagagaggac     4380
aggaagtaaa tgggagttat ttccagaaca gggcagggat gtagctctgt ggtagagcac    4440
acagatgcgt ccccagcatg accaaagaca ccactaacag gaacacagat attttcacca    4500
ctaacaggaa cacagacatt ttctgaatta acagtagcag agtaccttgg cttttttgttt    4560
ttttatttac ttatttgtta ttgtttgggg ttgttttttgg ttttggtttt tctttctttt    4620
tttttttaaga ttttatttat ttattatgta tacaacattg tatatttgca caccagaaga   4680
gggaaccaga tctcataatg gatggttgtg agccaccatg tggttgctgg gaattgaact    4740
ctggacctct ggaagagcag tcagcactct aacctctga gccatctatc cagcccttg     4800
gttttggttt tcaagcagg gattctctgt cctgtagctt acattgtaga ctaggatggc     4860
ctggaactct cagagatccc ctcacctctg cctcctgagt gctgggatta aaggtgtgtg    4920
acaccaccac ctagcaattt gtacattatt atctcatttc tccattacta taatcctgtg    4980
aagataccag cactcagaga agccatgcaa cttgcctaag gacacatagt tctgaattc     5039
```

<210> SEQ ID NO 2
<211> LENGTH: 1651
<212> TYPE: DNA
<213> ORGANISM: Cricetulus griseus

<400> SEQUENCE: 2

```
ctgcagttca gatttgagtg tcacaggcat tgtttctgag gctctctggg aaacgtactc      60
cttctctaca ggagcctggc gtctggctgg agaaagactg agtgcctgag ggttgtttca    120
gaggcaccaa tcaatactca ccattaggac aacaactcca cgcatcacta aactttgacc    180
tccgtgctcc agagaggtcc caagatgcca attgatgcac aggccatata catagtccat    240
gaatgcaatg ccttcataga ctcctgtgaa ttaaatcata gagactttag caatggcaac    300
ataatgttgt taatgtacta gcaagcctgg aatgtgtaca gagaatgcct ggattaaagc    360
tgtgatggta tttgtgcctt taagaaaggc ttgtgtcttt aaaaaggtct tgaggataaa    420
ttctgcattc agaatgttgg ctagctgtca ctgtcctcta tatgactggg tggtgctggc    480
ataagatgtc ttgtaagcca gacatgaaat aagcacttgt gtgtagcccc aagacccaac    540
aacaagcttg agtacacacc cttcctagaa atcagaagac aggccaagaa gacctttaag    600
tgtgtttctc ttttatgtga aactttgtgg attttatttc cccagaaatg cgttttgggg    660
ggacttcttc attatggtct attgtcacat aaattgtgct cttcacagaa aagggtgatg    720
aaaccctgtt ccttgactgg gttgagtggg atccactgcc aaacagctgt ctgggctaaa    780
acagaatagc tgatttggaa agacttaaaa gggtaatcat tttgatgttg gtgggagttc    840
gtatctgaat gccatgttat agcttcttat atccaatcag aatggtccac atgtatgccc    900
tgtgtgccaa cagaggtctc cagtgcctcc tataagaagg ctagcaggaa gagaagacat    960
```

-continued

```
gaagtccatt gaagaaaaag ttacagactt caaaagcacc aaaaatcact gggaaccaaa       1020
gcaagtttcc cactatcccc gccccccccc ttgctggttt cttctgaaat gttatgcctc       1080
ttgataattg gcctgcccaa ggttgcaacc ttcatgtgcc ttgggtccat ttcacttcta       1140
gctctttaag tatataaata aatagataat tagatgatgg agtaggctct gtgggcttta       1200
cttcattcat ctggctcctg aacttgaatc caggcccatt tgaaatccca gggaaggttt       1260
tggctgggtg tgggggcata gctgtgttcc agttggctga ctcttcacct ggtagagagg       1320
acaggaagta aatgggagtt atttccagaa cagggcaggg atgtagctct gtggtagagc       1380
acacagatgc gtccccagca tgaccaaaga caccactaac aggaacacag atattttcac       1440
cactaacagg aacacagaca ttttctgaat taacagtagc agagtaccct tggcttttgt       1500
ttttttattt acttatttgt tattgtttgg ggttgttttt ggttttggtt tttcttcttt      1560 tttttttaa gattttattt atttattatg tatacaacat tgtatatttg cacaccagaa       1620
gagggaacca gatctcataa tggatggttg t                                     1651
```

<210> SEQ ID NO 3
<211> LENGTH: 23
<212> TYPE: DNA
<213> ORGANISM: Escherichia coli

<400> SEQUENCE: 3
cggtcagcct tgccttgttg tag                                              23

<210> SEQ ID NO 4
<211> LENGTH: 29
<212> TYPE: DNA
<213> ORGANISM: Homo sapiens

<400> SEQUENCE: 4
gcatctccag gcaaagccac tgaggtccg                                        29

<210> SEQ ID NO 5
<211> LENGTH: 30
<212> TYPE: DNA
<213> ORGANISM: Homo sapiens

<400> SEQUENCE: 5
cacggagcat gagaagacgt tcccctgctg                                       30

<210> SEQ ID NO 6
<211> LENGTH: 21
<212> TYPE: DNA
<213> ORGANISM: Cricetulus griseus

<400> SEQUENCE: 6
ctagcctgcc tcacaagctt g                                                21

<210> SEQ ID NO 7
<211> LENGTH: 21
<212> TYPE: DNA
<213> ORGANISM: Cricetulus griseus

<400> SEQUENCE: 7
gagtcagcct gagatacata g                                                21

<210> SEQ ID NO 8
<211> LENGTH: 23
<212> TYPE: DNA

-continued

<213> ORGANISM: Cricetulus griseus

<400> SEQUENCE: 8
gcatttcagc atggttggct agc                                    23

<210> SEQ ID NO 9
<211> LENGTH: 23
<212> TYPE: DNA
<213> ORGANISM: Cricetulus griseus

<400> SEQUENCE: 9
ggacttcatg tcttctctcc tgc                                    23

<210> SEQ ID NO 10
<211> LENGTH: 19
<212> TYPE: DNA
<213> ORGANISM: Cricetulus griseus

<400> SEQUENCE: 10
agcctatctc cattcgtca                                         19

<210> SEQ ID NO 11
<211> LENGTH: 32
<212> TYPE: DNA
<213> ORGANISM: Cricetulus griseus

<400> SEQUENCE: 11
ccgccgaatt catgtctgtg ttcctgttag tg                          32

<210> SEQ ID NO 12
<211> LENGTH: 19
<212> TYPE: DNA
<213> ORGANISM: Cricetulus griseus

<400> SEQUENCE: 12
agcctatctc cattcgtca                                         19

<210> SEQ ID NO 13
<211> LENGTH: 31
<212> TYPE: DNA
<213> ORGANISM: Cricetulus griseus

<400> SEQUENCE: 13
ccgccgaatt caaccacatg gtggctcaca a                           31

<210> SEQ ID NO 14
<211> LENGTH: 24
<212> TYPE: DNA
<213> ORGANISM: Escherichia coli

<400> SEQUENCE: 14
ggtcctgcaa ctttatccgc ctcc                                   24

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 15
cgtgtacggt gggaggtcta                                        20

```
<210> SEQ ID NO 16
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 16
aattgctacg tggtggtgtc                                              20

<210> SEQ ID NO 17
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 17
ggctgactct tcactggtag                                              20

<210> SEQ ID NO 18
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 18
acagagccta ctccatcatc                                              20

<210> SEQ ID NO 19
<211> LENGTH: 16
<212> TYPE: DNA
<213> ORGANISM: Artificial sequence
<220> FEATURE:
<223> OTHER INFORMATION: Oligonucleotide primer

<400> SEQUENCE: 19
gtcttcttgg cctgtc                                                  16

<210> SEQ ID NO 20
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 20
gtgcttattt catgtctggc                                              20

<210> SEQ ID NO 21
<211> LENGTH: 16
<212> TYPE: DNA
<213> ORGANISM: Artificial sequence
<220> FEATURE:
<223> OTHER INFORMATION: Oligonucleotide primer

<400> SEQUENCE: 21
tgacggattg cttcag                                                  16

<210> SEQ ID NO 22
<211> LENGTH: 20
<212> TYPE: DNA
<213> ORGANISM: Artificial sequence
<220> FEATURE:
<223> OTHER INFORMATION: Oligonucleotide primer
```

-continued

```
<400> SEQUENCE: 22
catctcgcac ctctatcagt                                            20

<210> SEQ ID NO 23
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 23
ggcctcagag tccatactgt                                            20

<210> SEQ ID NO 24
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 24
tctccacagc gactgcacta                                            20

<210> SEQ ID NO 25
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 25
gactgtagct cagtggtaga                                            20

<210> SEQ ID NO 26
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 26
ttcgagggag cacgcgaca                                             19

<210> SEQ ID NO 27
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 27
atccttggcc actggcctat                                            20

<210> SEQ ID NO 28
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 28
atgtctgtgt tcctgttagt g                                          21

<210> SEQ ID NO 29
<211> LENGTH: 18
```

```
<212> TYPE: DNA
<213> ORGANISM: Artificial sequence
<220> FEATURE:
<223> OTHER INFORMATION: Oligonucleotide primer

<400> SEQUENCE: 29
ccggtcacat tgtgttca                                               18

<210> SEQ ID NO 30
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 30
catctcgcac ctctatcagt                                             20

<210> SEQ ID NO 31
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 31
ggcatacatg tggaccattc                                             20
```

EXPRESSION VECTORS CONTAINING HOT SPOT FOR INCREASED RECOMBINANT PROTEIN EXPRESSION IN TRANSFECTED CELLS

This application is a continuation-in-part application of U.S. patent application Ser. No. 09/386,816, filed Aug. 31, 1999, now U.S. Pat. No. 6,521,419, which claims the benefit of U.S. Provisional Application Serial No. 60/101,292, filed Sep. 22, 1998, the contents of all of which are incorporated by reference herein in their entirety.

BACKGROUND OF THE INVENTION

Development of expression systems for the production of recombinant proteins is important for providing a source of a given protein for research or therapeutic use. Expression systems have been developed for both prokaryotic cells such as E. coli, and for eukaryotic cells, which include both yeast and mammalian cells. Expression in mammalian cells, for example Chinese hamster ovary (or "CHO") cells, is often preferred for the manufacture of therapeutic proteins, since post-translational modifications in such expression systems are more likely to resemble those found in human cells expressing proteins than the type of post-translational modifications that occur in microbial (prokaryotic) expression systems.

Transcription of eukaryotic genes is regulated by a variety of cis- and transacting regulatory elements. (Dillon et.al., (1993) Trends Genet. 9:134). Two of the best characterized cis-elements are promoters and enhancers. Promoters are DNA sequences immediately 5' to the coding sequence of the gene and encompass multiple binding sites for transacting transcription factors, forming the basic transcription apparatus. Enhancers are also composed of multiple binding sites for transacting transcription factors but can be found far upstream or downstream of coding sequences or even within introns. These elements can also act in an orientation independent manner. Activities of promoters and enhancers can be detected in transient expression systems and they contain elements which may or may not be tissue specific.

Another category of cis-acting regulatory elements are ones which are believed to regulate the chromatin structure including locus control regions ("LCRs") (Grosveld et.al., (1987) Cell 51:975), matrix attachment regions ("MARs") (Phi-Van et.al., (1990) Mol. Cell. Biol. 10:2302), scaffold attachment regions ("SARs") (Gasser & Laemmli (1987) Trends Genet. 3:16), insulator elements (Kellum & Schedl (1991) Cell 64:941) and Nuclear matrix-Associating DNAs (Bode J et.al., (1992) Science 255:195). MAR's and SAR's are similar to enhancers in that they are able to act over long distances, but are unique in that their effects are only detectable in stably transformed cell lines or transgenic animals. LCRs are also dissimilar to enhancers in that they are position and orientation dependent, and are active in a tissue specific manner.

Recombinant expression plasmids comprising a gene of interest that encodes all or a portion of a desired protein are routinely used to generate stable CHO cells or transfectomas, expressing the desired recombinant protein. These recombinant plasmids randomly integrate into the genome of the host producing recombinant proteins. However, the frequency of transfectomas carrying the stably integrated recombinant gene that are capable of expressing a desired recombinant protein at high levels is quite low. Usually a large number of stably transfected mammalian transfectomas must be screened to identify clones which express the recombinant proteins at high levels. This is widely believed to be due to the effects of the genomic environment (hot spot) and the plasmid copy number, especially in light of the large size of the mammalian genome and the fact that only 0.1% of the genomic DNA contains transcriptionally active sequences. (Little (1993) Nature 366:204). It is highly unlikely that the current technology of random plasmid integration into the genome of CHO cells will result in the insertion of a recombinant gene into a transcriptional hot spot that is capable of gene amplification leading to high levels of gene expression.

Expression augmenting sequences have been disclosed to increase expression of recombinant protein (Morris, A., et.al., Expression augmenting elements (EASE) for eukaryotic expression systems: WO 97/25420). An increase in the frequency of high-level recombinant gene expressing cell lines would provide a much greater pool of high protein expressing transfectomas to choose from. This task can be accomplished by generating homologous recombinant plasmids targeted to a transcriptional hot spot and devising a means to select for such transfectomas.

SUMMARY OF THE INVENTION

Novel transcription regulatory sequences, referred to herein as HIRPE (Hot spot for Increased Recombinant Protein Expression), that facilitate increased expression of recombinant proteins in mammalian host cells, are disclosed. A preferred embodiment of the invention is a HIRPE that was obtained from CHO cell genomic DNA.

The present invention discloses a HIRPE from a genomic locus in the CHO genome that is capable of high recombinant gene expression. These loci contain sequence elements that define origin of replication, gene amplification, and MARs in the mammalian genome. In a most preferred embodiment of the invention, the HIRPE is selected from the group consisting of: (a) DNAs comprising nucleotides 1 through 5039 of SEQ ID NO: 1; (b) fragments of SEQ ID NO: 1 that have HIRPE activity; (c) nucleotide sequences complementary to (a) and/or (b); (d) nucleotide sequences that are at least about 80%, more preferably about 90%, and more preferably about 95% identical in nucleotide sequence to (a), (b) and/or (c) and that exhibit HIRPE activity; and (e) combinations of the foregoing nucleic acid sequences that exhibit HIRPE activity.

Expression vectors comprising the novel HIRPE are able to transform CHO cells to increase expression of recombinant proteins. Thus, another embodiment of the invention is an expression vector comprising a HIRPE. In a preferred embodiment, the expression vector further comprises a eukaryotic promoter/enhancer driving the expression of all or a portion of a protein of interest. Two or more expression vectors may be used to transfect a cell (e.g., CHO cell), wherein each vector comprises a nucleic acid sequence encoding different polypeptides that assemble (when expressed) to form a desired protein. In a more preferred embodiment, the expression vector comprises a plasmid wherein a first exon encodes a gene of interest and a second exon encodes an amplifiable dominant selectable marker. A preferred marker is dihydrofolate reductase ("DHFR"); other amplifiable markers are also suitable for use in the inventive expression vectors.

Mammalian host cells can be transformed with an expression vector of the present invention to produce high levels of recombinant protein. Accordingly, another embodiment of the invention provides a mammalian host cell transformed with an expression vector of the present invention. Also within the scope of the present invention are mammalian host cells transformed with two expression vectors, wherein each of said two expression vectors encodes a polypeptide subunit that when coexpressed assembles into a desired protein with biological activity. In a most preferred embodiment, the host cells are CHO cells.

The invention also provides a method for obtaining a recombinant protein, comprising transforming a host cell with an expression vector of the present invention, culturing the transformed host cell under conditions promoting expression of the protein, and recovering the protein. In a preferred application of the invention, transformed host cells are selected with two selection steps, the first to select for cells expressing the dominant amplifiable marker, and the second step for high expression levels and/or amplification of the marker gene as well as the gene of interest. In a preferred embodiment, the recombinant protein comprises CTLA4-Ig or a variant thereof, such as substitution, addition and deletion variants to the amino acid sequence to produce different forms of a CTLA4-Ig molecule. For an extensive review of CTLA4, CTLA4 variants such as LEA29Y and L104E, and CTLA4 fusion proteins (e.g., CTLA4-Ig) see WO 93/00431 and WO 01/92337.

In another embodiment, the expression vectors of the present invention can be used to produce antibodies, for example, anti-CD40 antibody.

BRIEF DESCRIPTION OF THE FIGURES

FIG. 1 shows cloning of the CTLA4-Ig integration site in the parental CTLA4-Ig expressing cell line, referred to herein as cell line "P".

FIG. 8 shows the effect of the A-T rich motif region on recombinant gene expression. The figure gives CTLA4-Ig expression in $\mu$g/ml from the top four transfectomas which contain either the full length 5.0 kb nucleic acid sequence; 1.6 kb of nucleic acid sequence (which includes the A-T rich motif); or a 1.4 kb region which does not include the A-T rich motif.

FIG. 9 shows the oligonucleotides used to obtain the HIRPE of the present invention.

DETAILED DESCRIPTION OF INVENTION

Figure 1A:
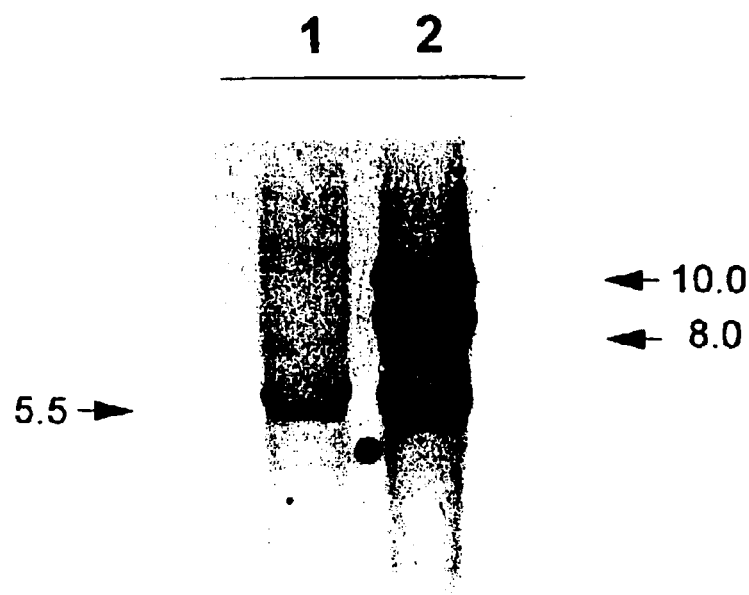
FIG. 1A shows a Southern blot in which a 5.5 kb EcoRI fragment represents the native chromosome in both the DG44 host and P CHO cell lines. The 8.0 kb and 10.0 kb bands in lane 2 represent the rearranged left and right flanking regions respectively.
Figure 1B:
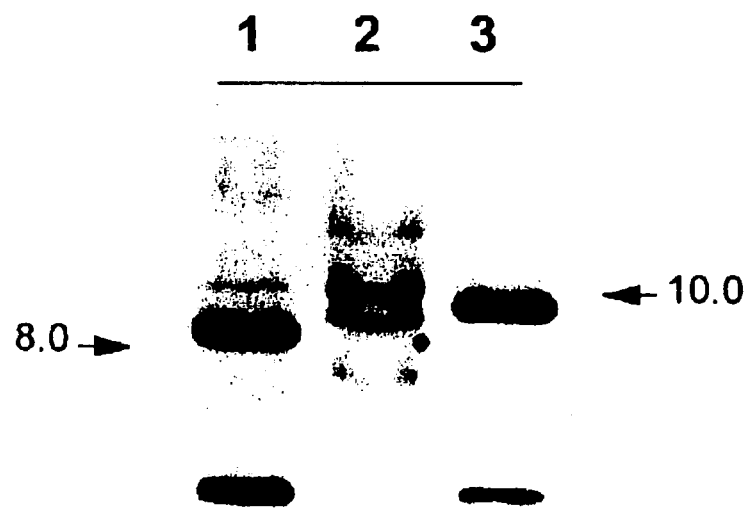
FIG. 1B shows that the cloned EcoRI fragments containing the left flanking (lane 1) and right flanking (lane 2) regions of the cell line P integration site co-migrate with EcoRI digested genomic DNA from cell line P.

Applicants have isolated and identified novel sequence elements that can improve expression of reporter proteins two to ten fold in stable cell pools when inserted in an expression vector. We refer to these novel sequence elements as HIRPE (Hot spot for Increased Recombinant Protein Expression).

A DNA clone containing a nucleic acid molecule of the present invention was deposited with the American Type Culture Collection ("ATCC") (10801 University Blvd., Manassas, Va. 20110-2209) on Aug. 25, 1998, as ATCC Deposit/Accession No. 203153. The deposit(s) referred to herein will be maintained under the terms of the Budapest Treaty on the International Recognition of the Deposit of Microorganisms for purposes of Patent Procedure. This deposit is provided merely as convenience to those skilled in the art and is not an admission that a deposit is required under 35 U.S.C. §112. The sequence of the polynucleotides contained in the deposited materials is incorporated herein by reference and is controlling in the event of any conflict with any description of sequences herein. A license may be required to make, use or sell the deposited materials, and no such license is hereby granted.

The present invention relates to the identification of a recombinant protein integration site in a CHO cell host genome, and the construction of homologous recombination vectors for achieving the high recombinant gene expression in CHO cells. More particularly, the present invention relates to the identification of a CTLA4-Ig integration site in the CHO DG44 host genome.

HIRPE activity was identified in flanking regions on both ends of a gene encoding a protein of interest. As explained in detail below, the flanking regions were separated and sequenced to determine the novel HIRPE sequence disclosed herein. The DNA primers used to obtain the HIRPE sequence are detailed in FIG. 9 (SEQ ID NOS: 15–31). The novel HIRPE sequence of the present invention comprises the following nucleic acid sequence (SEQ ID NO: 1):

```
TAGGCTAGCC TGCCCACAAG CTTCCTGGCT CCTCCTAACA TCTCCCTTTA      50
AATCACTGGG CTCACCAACA TTCCTGCTGC AGTGTCAGGT TTGTTCCTGA     100
CTTTAGGGAT TCAAACTCAG GTCCTCACAC TTGTGTTGCA AAAGCTTACT     150
CAGAGAGTCA TCTGCTCACA CCCGGCTGTT TGTGTTTTGA GACAGGGTCT     200
CCCTATGTAT CTCAGGCTGA CCTCCAACTG ACTCCCTTCC TCCTAACTGC     250
CTCCCTAGTG CTAGGATCCC AGGCCTTTCT TCCCATGATT CTGGGAAAGG     300
CAAGACTAGG GACAACTCCC TGGTATACTG AGGGCTCCTG CAGGGACCCT     350
TGCATCCCAT CCTTGGCCAG TGGCCTATAG GGACTCCCTG TGATCCCTGC     400
TTTCTAGCAT TGCCCTGCTC CACTCAGTTC TTGTTACTTT AATCACTTCC     450
AACATTAAGT TTTTGAAAAA TTGCAGTTTC TACCCTGAGA ACATACACAA     500
ATGACTCATG GGCGAGAAGA CTCTCAGTGC CCACATCATT GCAGAGATTC     550
AGATCAAAAC TCCAGTGAGT CATCACTTCA ACCCCCTGGG AAGAGCACAT     600
CAAAAACAAT TCTTTTCTTT TCTTCTCTTT TCTTTTCTTT TCTTTCTTTT     650
TCTGACAACA CTGGGGATTG AGTCTAAGGC CTCATGCACC TTAGGCAAGC     700
GCTCTACCAC TGAGCTACAG TCCTAACTTT TTTTTTTCTT TTTAAGAACA     750
ATAAAAAACA AAAACAAAAT ATAAAACAAG GAAACATGG AGGCACATGC      800
TGGTAATCCC AACACTACAG AGGCAAAGAC AGAGGCAGGA AGGACATAAT     850
AAATTCCAGA CCAGCTGGTG TTAGAATGAG ACCCTGTCTC AGAAAGAAAG     900
AAAAAAAAGA AAGAAAGAAA GAAAGGAAGA AAGAAAGAAA GAGGGAGGGA     950
GGAGGGAGAA AGAGAGGAAT GGGCAAGGAT GTAGAGAGAC GAGAAACTTT    1000
GTGCACTATC ATGAAAGCAA AATAGTGCAG TCGCTGTGGA GAATGGTATG    1050
GTAATGCTGG AAAGAAGGCT CATCGAGGAA ATGACCTTGC AACCAAACCC    1100
GAAGACCTGA GTTTGATCCC TGATACCTAC ATGGTAGAAG AACTAACTCT    1150
ATCAAGTAGT CCTTTGACTT CCAAATGTAT GCTGTGGCAC ATACAGTCCT    1200
CTTCCCCCAA TAAATAATGT AATTAAAAAA AGAAAAGGGG CTGGAGAGAT    1250
GGCTCAGTGG TTAAGAGCAT TGGCTCTTAA TCCAGAGAAC CCGGGTTCAA    1300
TTCCCAGCAC CCACATAGCA GCTTACAACT GCCTCCAGGG GGTCCAACAC    1350
CCTCACACAG ACATACACAC AGATAAACAG CAATGTACAT AAAATAAATA    1400
AATTATTTTT AACAACAACA AAAAAAAATG AAAAGAAAAG AAGGCTGGGC    1450
AGTGGTGGCA CACCACATAC CTTTAGTCTT TGTACTCAGG AGTCAGAGAC    1500
CGGCAGATCT CTGTGAGTTT GAGGCCAGCC TGGTCTACAA AGCAAGTTCC    1550
AGAACATCCA GGGCTGTTAC ACAGAGAAAC CTCAAAATAA AATAAAATAA    1600
AATAAAATAA AATGGAAGAA ACAAACAAAG AAAGAAAGAA AGAAGAAAAG    1650
AAAAGTGAAA AAGAGCATGA TAGTTCTTCA GAAAGTTAAG CGTTGCTACT    1700
GATGGTGGCC TGAAGTCCTG TCTTCAATAC TCCACAATAA GTAATAGTGT    1750
GCAAACAAGT ACATAATCCA GCTAAGCACT AAATTACCCA TGATCTTCCT    1800
CTTTGGTGTA TACCTCAAAG AGTTGACAGG CAGCCTTATT AGAGTGACAT    1850
TGTCTTTAAA CCCAGCATGA CCATCCTGAT GAACTGCTGT GATGCCCAGG    1900
GAAGACAGGG TAACCTCGAA GTCCAAGTAC TTCCTTAAGA CCATTTAACT    1950
TCTGGATGAT TATTAAAAAT GCTTCATTGT AGGAGCAGAC AGTATGGACT    2000
```

-continued

```
CTGAGGCCAT CAGCAGATTG CATATCCCTT CAAGGGAAGA CTGTGGGGCT      2050

GATGGGCAAG AAACCAAAAT AGCTAACAAG AGCTATTTAA GGCAGGAAGA      2100

GTCCATGTTG GTTTGCAGTT CAAGGGTACA GTCCATCACG GTGAAGAAGA      2150

CAAGATGGCA GAAGCATGGG GCAACCGGTC ACATTGTGTT CACCAACAGG      2200

AAACAGAAAA CAACAAATGC CGTGCTGGGC TCACTTTCTC CTTTTTTCCT      2250

TTTCATTCAG CTTGGAACTG CTACCCGTGA GATGATGCCA CCCATGTTCA      2300

GGGTAGATCT TCCCTTTTTT TGTTGAGCTT CTCTAGAAAT ACCCTCAAAG      2350

ACACATACAG TAGTATGCCT CCCAGAGGAC TCTAATTGCA ATGTAGTTGA      2400

CAAGGAAGTT TAACCATCAT AGCCGGCAAA CCTAGGGTTG ATACCTTTAA      2450

TATAGATTCC TTTCGGTAGT CTGAGTATGC CTAGTCTAAT GCTTGAGTCT      2500

TCGAAAAGAA CTCCAGCTGG AGGCTGAGAG ATTCATTGGT GCACGTTGCA      2550

GTTTGCATGG GGAGAGGCTG CTGTCTGTGG CTGAAGGGAG CAGTGTGCAG      2600

AGTATGAGGA TGAATAGGAG AAGAGCTAGG TGCAAAGTCC ACCGTCCACT      2650

TGTCACGGGG CCCCTGGATG ACCACCATCA AGGAAATGGA GACCAATACC      2700

TGAAAGGGTT TGAGTATGGC CAATGAGGCA GAAGAAATTG AGAGTGAGTC      2750

AACCCTAGAG GAAGATCTAC AACTCTGCTG ACCCCATGAT GTTGACCTTA      2800

TGAAGCTAAA ACATAATAAA TGGACTTCCA CTGATAGAGG TGCAAGATGA      2850

ACAAGCCTAT CTCATTCGTC AGTCACTGAA CTTGGGATGA TCTGTTAGGG      2900

CAGCAACAGA AAACTAATAT AAATATATAT GTATATGATA TTTATTGGTT      2950

TTTCAGTACT TTCCTAGTGA GAGTCATTGC TATGCAGATA TTGCACGATG      3000

CTATTTATCA CTTTCCACTT ACCCAGCTGA AGCAATCCGT CACTATCTGA      3050

GAGCCTCTCT GCAGTTCAGA TTTGAGTGTC ACAGGCATTG TTTCTGAGGC      3100

TCTCTGGGAA ACGTACTCCT TCTCTACAGG AGCCTGGCGT CTGGCTGGAG      3150

AAAGACTGAG TGCCTGAGGG TTGTTTCAGA GGCACCAATC AATACTCACC      3200

ATTAGGACAA CAACTCCACG CATCACTAAA CTTTGACCTC CGTGCTCCAG      3250

AGAGGTCCCA AGATGCCAAT TGATGCACAG GCCATATACA TAGTCCATGA      3300

ATGCAATGCC TTCATAGACT CCTGTGAATT AAATCATAGA GACTTTAGCA      3350

ATGGCAACAT AATGTTGTTA ATGTACTAGC AAGCCTGGAA TGTGTACAGA      3400

GAATGCCTGG ATTAAAGCTG TGATGGTATT TGTGCCTTTA AGAAAGGCTT      3450

GTGTCTTTAA AAAGGTCTTG AGGATAAATT CTGCATTCAG AATGTTGGCT      3500

AGCTGTCACT GTCCTCTATA TGACTGGGTG GTGCTGGCAT AAGATGTCTT      3550

GTAAGCCAGA CATGAAATAA GCACTTGTGT GTAGCCCCAA GACCCAACAA      3600

CAAGCTTGAG TACACACCCT TCCTAGAAAT CAGAAGACAG GCCAAGAAGA      3650

CCTTTAAGTG TGTTTCTCTT TTATGTGAAA CTTTGTGGAT TTTATTTCCC      3700

CAGAAATGCG TTTTGGGGGG ACTTCTTCAT TATGGTCTAT TGTCACATAA      3750

ATTGTGCTCT TCACAGAAAA GGGTGATGAA ACCCTGTTCC TTGACTGGGT      3800

TGAGTGGGAT CCACTGCCAA ACAGCTGTCT GGGCTAAAAC AGAATAGCTG      3850

ATTTGGAAAG ACTTAAAAGG GTAATCATTT TGATGTTGGT GGGAGTTCGT      3900

ATCTGAATGC CATGTTATAG CTTCTTATAT CCAATCAGAA TGGTCCACAT      3950

GTATGCCCTG TGTGCCAACA GAGGTCTCCA GTGCCTCCTA TAAGAAGGGC      4000
```

-continued

| | | | | |
|---|---|---|---|---|
| TAGCAGGAGA | GAAGACATGA | AGTCCATTGA | AGAAAAAGTT | ACAGACTTCA | 4050
| AAAGCACCAA | AAATCACTGG | GAACCAAAGC | AAGTTTCCCA | CTATCCCCGC | 4100
| CCCCCCCCTT | GCTGGTTTCT | TCTGAAATGT | TATGCCTCTT | GATAATTGGC | 4150
| CTGCCCAAGG | TTGCAACCTT | CATGTGCCTT | GGGTCCATTT | CACTTCTAGC | 4200
| TCTTTAAGTA | TATAAATAAA | TAGATAATTA | GATGATGGAG | TAGGCTCTGT | 4250
| GGGCTTTACT | TCATTCATCT | GGCTCCTGAA | CTTGAATCCA | GGCCCATTTG | 4300
| AAATCCCAGG | GAAGGTTTTG | GCTGGGTGTG | GGGGCATAGC | TGTGTTCCAG | 4350
| TTGGCTGACT | CTTCACCTGG | TAGAGAGGAC | AGGAAGTAAA | TGGGAGTTAT | 4400
| TTCCAGAACA | GGGCAGGGAT | GTAGCTCTGT | GGTAGAGCAC | ACAGATGCGT | 4450
| CCCCAGCATG | ACCAAAGACA | CCACTAACAG | GAACACAGAT | ATTTTCACCA | 4500
| CTAACAGGAA | CACAGACATT | TTCTGAATTA | ACAGTAGCAG | AGTACCTTGG | 4550
| CTTTTTGTTT | TTTTATTTAC | TTATTTGTTA | TTGTTTGGGG | TTGTTTTTGG | 4600
| TTTTGGTTTT | TCTTTCTTTT | TTTTTTAAGA | TTTTATTTAT | TTATTATGTA | 4650
| TACAACATTG | TATATTTGCA | CACCAGAAGA | GGGAACCAGA | TCTCATAATG | 4700
| GATGGTTGTG | AGCCACCATG | TGGTTGCTGG | GAATTGAACT | CTGGACCTCT | 4750
| GGAAGAGCAG | TCAGCACTCT | TAACCTCTGA | GCCATCTATC | CAGCCCCTTG | 4800
| GTTTTGGTTT | TTCAAGCAGG | GATTCTCTGT | CCTGTAGCTT | ACATTGTAGA | 4850
| CTAGGATGGC | CTGGAACTCT | CAGAGATCCC | CTCACCTCTG | CCTCCTGAGT | 4900
| GCTGGGATTA | AAGGTGTGTG | ACACCACCAC | CTAGCAATTT | GTACATTATT | 4950
| ATCTCATTTC | TCCATTACTA | TAATCCTGTG | AAGATACCAG | CACTCAGAGA | 5000
| AGCCATGCAA | CTTGCCTAAG | GACACATAGT | TCTGAATTC | | 5039

Additionally, the present invention encompasses fragments of SEQ ID NO: 1 that also exhibit HIRPE activity. A preferred example of a fragment useful in the present invention is a 1.6 kb sequence comprising nucleotides 3059 through 4709 of SEQ ID NO: 1 (said preferred fragment shown in SEQ ID NO: 2).

Expression vectors comprising the isolated 5.0 kb sequence (SEQ ID NO: 1) and shorter fragments thereof were able to transform CHO cells and result in high levels of protein expression. The present novel HIRPE is useful to improve expression of a recombinant protein driven by a promoter/enhancer region to which it is linked.

Moreover, additional fragments of SEQ ID NO: 1 exhibiting HIRPE activity can be identified, as well as similar HIRPE motifs from other types of cells or from other integration sites in transformed cells. In addition, it is known in the art that subsequent processing of fragments of DNA prepared by restriction enzyme digestion can result in the removal of additional nucleotides from the ends of the fragments.

Other combinations of fragments of SEQ ID NO: 1 can also be developed, for example, sequences that include multiple copies of all or a part of SEQ ID NO: 1. Such combinations can be contiguously linked or arranged to provide optimal spacing of the fragments. Additionally within the scope of the present invention are expression vectors comprising the sequence of SEQ ID NO: 1 arranged with insertion sequences therein (e.g., insertion of a gene encoding a desired protein at a certain selected site in SEQ ID NO: 1).

The HIRPE disclosed herein was isolated from CHO cells. Homologous sequences that increase recombinant protein expression are expected to exist in cells from other mammalian species, as well as in cell lines derived from other tissue types, and can be isolated by techniques that are well known in the art, for example by cross-species hybridization or PCR-based techniques. In addition, changes can be made in the nucleotide sequence set forth in SEQ ID NO: 1 or SEQ ID NO: 2 by site directed or random mutagenesis techniques that are known in the art. The resulting HIRPE variants can then be tested for HIRPE activity as described herein. DNAs that are at least about 80%, more preferably about 90%, and more preferably about 95% identical in nucleotide sequence to SEQ ID NO: 1, or fragments thereof, having HIRPE activity are isolatable by routine experimentation and expected to have HIRPE activity. For fragments of SEQ ID NO: 1, percent identity refers to that portion of the reference native sequence that is found in the fragment. Accordingly, homologues of the disclosed HIRPE sequence and variants thereof are also encompassed by the present invention.

Recombinant expression vectors include synthetic or cDNA-derived DNA fragments encoding a protein, operably linked to suitable transcriptional or translational regulatory elements derived from mammalian, viral or insect genes. Such regulatory elements may include a transcriptional promoter, a sequence encoding suitable mRNA ribosomal binding sites, and sequences which control the termination of transcription and translation. Mammalian expression vectors may also comprise non-transcribed elements such as an origin of replication, a suitable promoter and enhancer linked to the gene to be expressed, other 5' or 3' flanking non-transcribed sequences, 5' or 3' non-translated sequences such as necessary ribosome binding sites, a polyadenylation site, splice donor and acceptor sites, and transcriptional termination sequences. An origin of replication that confers the ability to replicate in a host, and a selectable gene to facilitate recognition of transformants, may also be incorporated.

DNA regions are operatively linked when they are functionally related to each other. For example, a promoter is operatively linked to a coding sequence if it controls the transcription of the sequence; or a ribosome binding site is operatively linked to a coding sequence if it is positioned so as to permit translation. Transcriptional and translational control sequences in expression vectors used in transforming cells are known in the art.

Transformed host cells are cells which have been transformed or transfected with expression vectors constructed using recombinant DNA techniques and which contain sequences encoding all or a portion of recombinant proteins. Expressed proteins will preferably be secreted into the cell culture supernatant, depending on the DNA selected, but may be deposited in the cell membrane. Various mammalian cell culture systems can be employed to express recombinant protein, all well known in the art, for example COS lines of monkey kidney cells, CHO cells, HeLa cells, and BHK cell lines.

A commonly used cell line is DHFR$^-$ CHO cell line which is auxotrophic for glycine, thymidine and hypoxanthine, and can be transformed to the DHFR$^+$ phenotype using DHFR cDNA as an amplifiable dominant marker. One such known DHFR$^-$ CHO cell line is DKXB11 (Urlaub et.al., (1980) Proc. Natl. Acad. Sci. USA 77:4216). Other cell lines developed for specific selection or amplification schemes will also be useful with the novel HIRPE of the present invention.

Several transformation protocols are known in the art, and are reviewed, for example, in Kaufman et. al., (1988) Meth. Enzymology 185:537. The transformation protocol chosen will depend on the host cell type and the nature of the gene of interest, and can be chosen based upon routine experimentation. The basic requirements of any such protocol are first to introduce DNA encoding a protein of interest into a suitable host cell, and then to identify and isolate host cells which have incorporated the DNA in stable, expressible manner. Examples of methods useful for introducing DNA encoding a protein of interest can be found in Wigler et.al., (1980) Proc. Natl. Acad. Sci. USA 77:3567; Schaffner (1980) Proc. Natl. Acad. Sci. USA 77:2163; Potter et.al, (1988) Proc. Natl. Acad. Sci. USA 81:7161; and Shigekawa (1988) BioTechniques 6:742.

A method of amplifying the gene of interest is also desirable for expression of the recombinant protein, and typically involves the use of a selection marker. Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for). Several amplifiable markers are suitable for use in the present invention (for example, as described in Maniatis, Molecular Biology: A Laboratory Manual, Cold Spring Harbor Laboratory, N.Y. (1989)). Useful selectable markers for gene amplification in drug-resistant mammalian cells include DHFR-MTX (methotrexate) resistance (Alt et.al., (1978) J. Biol. Chem. 253:1357; Wigler et. al., (1980) Proc. Natl. Acad. Sci. USA 77:3567), and other markers known in the art (as reviewed, for example, in Kaufman et.al., (1988) Meth. Enzymology 185:537).

In a preferred embodiment, the recombinant protein comprises CTLA4-Ig or a variant thereof, such as substitution, addition and deletion variants to the amino acid sequence to produce different forms of a CTLA4-Ig molecule. Such forms of a CTLA4-Ig molecule are described in WO 93/00431 and WO 01/92337 incorporated herein by reference in their entirety. As used herein a "variant of CTLA4" or "CTLA4 mutant molecule" is a molecule that can be full length CTLA4 or portions thereof (derivatives or fragments) that have a mutation or multiple mutations in CTLA4 (preferably in the extracellular domain of CTLA4). CTLA4 variants can include the entire extracellular domain of CTLA4 or portions thereof which recognize and bind to CD80 and/or CD86. Variants of CTLA4 molecules may include a biologically or chemically active non-CTLA4 molecule therein or attached thereto. The CTLA4 variants may be soluble (i.e., circulating) or bound to a surface. Preferred CTLA4 variants produced in accordance with the present invention bind CD80 and/or CD86 with greater avidity than CTLA4.

The invention further provides a soluble CTLA4 variant having an amino acid sequence corresponding to a moiety that alters the solubility, affinity and/or valence of the CTLA4 variant for binding to the CD86 antigen.

In accordance with the practice of the invention, the moiety can be an immunoglobulin constant region or portion thereof. For in vivo use, it is preferred that the immunoglobulin constant region does not elicit a detrimental immune response in the subject. For example, in clinical protocols, it is preferred that mutant molecules include human or monkey immunoglobulin constant regions. One example of a suitable immunoglobulin region is human C(gamma)1. Other isotypes are possible. Furthermore, other weakly or non-immunogenic immunoglobulin constant regions are possible.

The invention also provides soluble variant CTLA4Ig fusion proteins preferentially reactive with the CD86 antigen compared to wildtype CTLA4, the protein having a first amino acid sequence consisting of the extracellular domain of CTLA4 mutant and a second amino acid sequence consisting of the hinge, CH2 and CH3 regions of a human immunoglobulin, e.g., Cγ1.

CTLA4 variants can be rendered soluble by joining a second molecule. The second molecule can function to enhance solubility of CTLA4 or as an identification tag. Examples of suitable second molecules include but are not limited to p97, env gp120, E7, and ova molecules (Dash, B. et al. J. Gen. Virol. 1994 June, 75 (Pt6): 1389–97; Ikeda, T., et al. Gene, Jan. 28, 1994, 138(1–2):193–6; Falk, K., et al. Cell. Immunol. 1993 150(2):447–52; Fujisaka, K. et al. Virology 1994 204(2):789–93). Examples of other second molecules are described in Gerard, C. et al. Neuroscience 1994 62(3):721; Byrn, R. et al. 1989 63(10):4370; Smith, D. et al. Science 1987 238:1704; and Lasky, L. Science 1996 233:209.

In a preferred embodiment of the present invention the recombinant protein of interest is a CTLA4 variant which binds CD80 and/or CD86 and comprises an extracellular domain of CTLA4 wherein (a) alanine at position 29 is substituted with an amino acid selected from the group consisting of tyrosine, leucine, tryptophan, and threonine, and (b) a leucine at position 104 is substituted with a glutamic acid.

A preferred CTLA4 variant is L104EA29YIg (also referred to as "LEA29YIg") having two amino acid changes. Particularly, the alanine residue at position 29 of CTLA4 is changed to tyrosine and the leucine residue at position 104 is changed to glutamic acid. Another preferred CTLA4 variant is L104EIg wherein the leucine residue at position 104 is glutamic acid. LEA29YIg and L104EIg bind CD80 and CD86 more avidly than CTLA4Ig.

CTLA4 variants with altered affinities for CD80 and/or CD86 can be synthesized and screened by generating a library of mutations at a specific codon of an extracellular portion of CTLA4 and then screening the mutant CTLA4 molecules, for example, using a surface plasmon resonance detector system that involves covalent binding of either CD80Ig or CD86Ig to a dextran-coated sensor chip located in the detector to identify mutants with altered reactivity to CD80 or CD86. The test molecule can then be injected into a chamber containing the sensor chip and the amount of complementary protein that binds can be assessed based on the change in molecular mass which is physically associated with the dextran-coated side of the sensor chip; the change in molecular mass can be measured by the detector system.

In another embodiment of the present invention, expression vectors containing HIRPE can be used to express a protein of interest comprising more than one polypeptide. In one embodiment, two nucleic acid sequences encoding different polypeptides are inserted in the vector and upon expression in a host cell the two polypeptides assemble into a protein of interest with biological activity. Alternatively, two expression vectors each containing a HIRPE sequence can be used to produce a protein of interest.

In accordance with the present invention, antibodies can be produced using the HIRPE expression vector. In this embodiment, one HIRPE expression vector includes a nucleic acid sequence encoding a heavy chain of an antibody and a nucleic acid sequence encoding a light chain of an antibody wherein said HIRPE expression vector encodes a polypeptide subunit that when coexpressed assembles into a desired antibody with biological activity. Alternatively, two expression vectors each containing a HIRPE sequence can be used to produce antibodies. In this embodiment, one expression vector includes a nucleic acid sequence encoding a heavy chain of an antibody and the second vector includes a nucleic acid sequence encoding a light chain of an antibody wherein each of said two expression vectors encodes a polypeptide subunit that when coexpressed assembles into a desired antibody with biological activity. For example, the HIRPE expression vector of the present invention can be used to produce anti-CD40 antibodies described, for example, in U.S. Pat. Nos. 6,051,228 and 6,312,693 incorporated herein by reference in their entirety.

The following examples are meant to be illustrative of an embodiment of the present invention and do not limit the scope of the invention in any way. All references cited herein, whether supra or infra, are hereby incorporated by reference in their entirety.

EXAMPLE 1

Identification of the HIRPE of the Present Invention

The CHO cell line P is a cell line expressing high level of CTLA4-Ig protein. This cell line was selected using the most preferred method of producing the mammalian cell lines involving random integration. The mammalian expression plasmid used to generate cell line P is a modified pCDNA3 plasmid (available through Invitrogen, Inc.). The DHFR gene was engineered into this vector to serve as a dominant selection marker. The recombinant gene expression cassette in this plasmid is driven by CMV promoter and BGH polyadenylation sequence. The genomic DNA analysis of cell line P suggested that the cell line has multiple copies of the stably integrated plasmid DNA. This plasmid DNA amplification resulted in the co-amplification of the DNA encoding for the CTLA4-Ig gene leading to a high CTLA4-Ig expressing cell line.

Those skilled in the art of generating CHO transfectomas using random integration vectors realize that vectors containing a DHFR gene as a selection marker have to integrate into a transcriptional hot spot and successfully amplify the gene copy number in order to generate a high expressing cell line. The percent of transfected cells that sufficiently amplify the gene is expectedly low since evidence in the literature suggests that genomic loci capable of gene amplification in mammalian genome are rare (Robbins (1981) Cell 23:29); McArthur (1991) J. Biol. Chem. 266:6000). The genomic locus adjacent to the CTLA4-Ig plasmid integration site in cell line P represented one of those unique loci with elements necessary for gene amplification and high transcriptional activity.

The construction of homologous recombination vectors for delivering recombinant genes to the genomic locus adjacent to CTLA4-Ig gene in CHO cells required the cloning of the flanking genomic DNA from cell line P and inserting the cloned fragment into an appropriate eukaryotic expression vector, using methods well known in the art (see, e.g., Yarnold et.al., (1994) Cancer Research 54:506; Adair (1989) Proc. Natl. Acad. Sci. USA 86:4574; Smith et.al., (1989) J. Mol Bio. 213:415). This task was accomplished by first mapping the size of the EcoRI generated DNA fragments flanking the integration site followed by the construction of a CHO genomic library in E. coli and isolation of individual plasmid DNA containing the genomic fragments.

Figure 7:
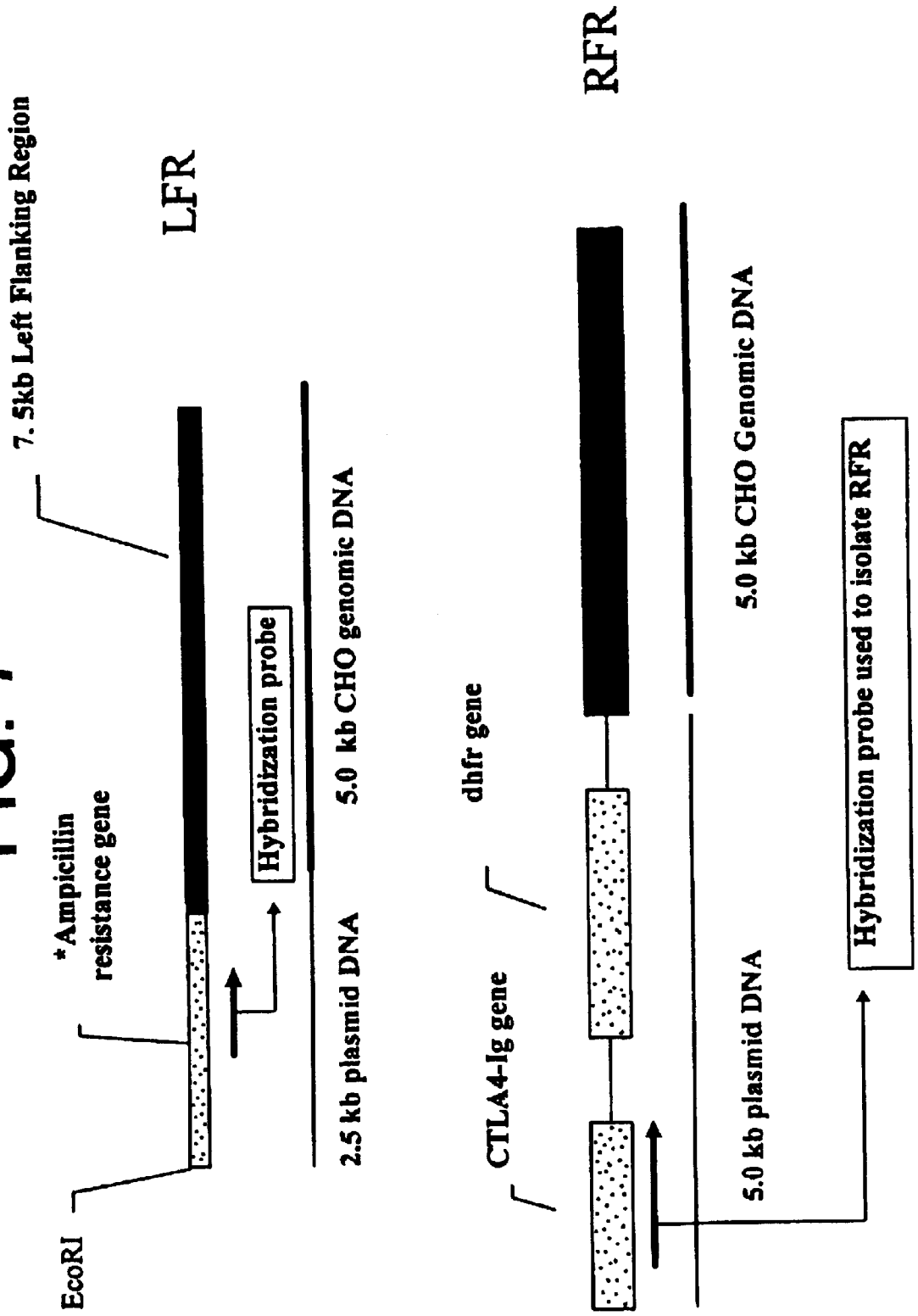
FIG. 7 shows a diagrammatic representation of the LFR and RFR fragments as analyzed by Southern blot analysis and restriction enzyme mapping.
Figure 10:
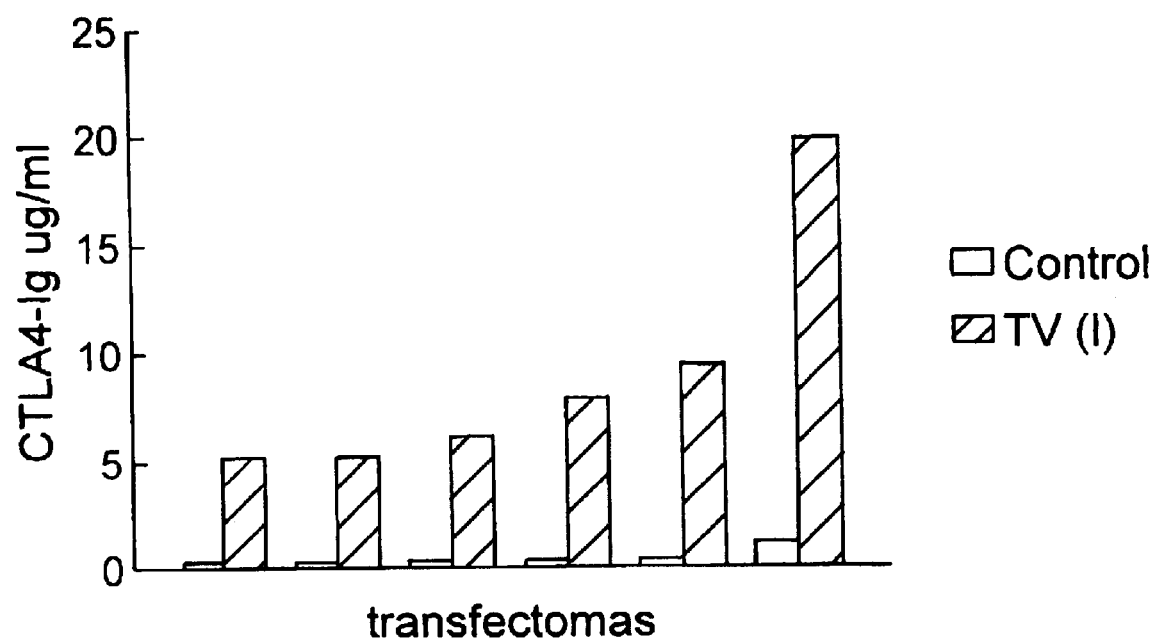
FIG. 10 shows that the HIRPE of the present invention enhances expression of CTLA4-Ig.
Figure 11:
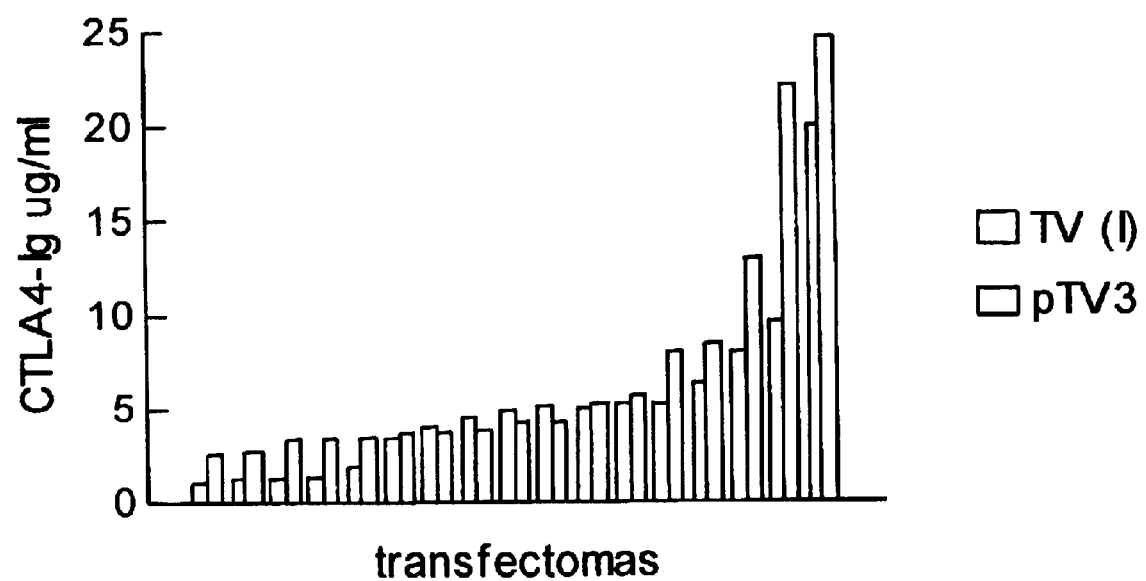
FIG. 11 shows that the insertional and replacement vectors produce similar results.

A Southern blot analysis facilitated mapping of the CTLA4-Ig integration site in CHO cells (FIG. 7). Applicants used a known strategy called "DNA walking" using Southern blot analysis to analyze the CTLA4-Ig integration site in CHO cell line P. The DNA walking procedure employed known plasmid DNA sequence to characterize unknown CHO genomic DNA flanking the plasmid sequence. To analyze the CTLA4-Ig integration site, approximately ten micrograms of CHO genomic DNA was digested with 100 units of EcoRI restriction enzyme (New England Biolabs). The restriction digested genomic DNA was subjected to agarose gel electrophoresis on 0.7% agarose gels at 15 volts for 12 hours. This process resolves the DNA by molecular size with high molecular weight DNA on the top.

The genomic DNA embedded in the agarose gels was denatured in 0.4 M NaOH for approximately 30 minutes and transferred to 0.45 micron nitrocellulose membrane (Boehinger and Mannaheim) for 90 minutes using vacum blotter (Bio-Rad). The blotted filter was neutralized in 2 × SSPE buffer and the DNA was cross linked to the membrane using a UV cross link apparatus (Stratagene, Inc., La Jolla, Calif., on setting C3 for 20 seconds). The 1.2 kb hybridization probe used in the Southern blot was a PCR fragment that was digoxigenin labelled using Boehringer Mannheim labelling kit. The PCR fragment was derived from the bacterial beta-lactamase gene and was prepared using the following oligonucleotide primers:

```
Forward primer:
GGTCCTGCAACTTTATCCGCCTCC;     (SEQ ID NO:14)

Reverse primer:
CGGTCAGCCTTGCCTTGTTGTAG.      (SEQ ID NO:3)
```

The digeoxigenin labelled DNA was detected using chemiluminescent detection kit (Boehringer Mannheim).

The nitrocellulose filter with the genomic DNA was hybridized with five microliters of the hybridization probe in 5 ml of Eazy hybridization buffer (Boehringer Mannheim) for 16 hours at 68° C. The filter was washed twice in 2 × SSC at 65° C. for 30 minutes and the filter was developed with chemiluminescent assay kit for 5 minutes (Boehringer Mannheim). This Southern blot analysis revealed a 7.5 kb CHO genomic Left Flanking Region ("LFR") that hybridized to the beta lactamase probe. The restriction mapping of the 7.5 kb fragment revealed that it contained a 2.5 kb plasmid DNA with beta lactamase gene and a 5.0 kb CHO genomic DNA. Similarly, the EcoR I digested CHO genomic DNA in Southern blots was probed with plasmid DNA containing the 0.9 kb CTLA4-Ig gene as a hybridization probe, generated using PCR reaction (PCR primers: Forward Primer: GCATCTCCAGGCAAAGCCACTGAG-GTCCG (SEQ ID NO: 4); Reverse Primer: CACGGAG-CATGAGAAGACGTTCCCCTGCTG (SEQ ID NO: 5)). The preparation of digeoxigenin labelled hybridization probe and the hybridization conditions were exactly identical to the conditions described above. However, since the hybridization probe used to study the right flanking region is derived from the CTLA4-Ig gene (instead of the beta-lactamase gene), the Southern blot analysis revealed a 10.0 kb Right Flanking Region ("RFR") DNA band. This hybrid DNA fragment contains a 5.0 kb of plasmid DNA (CTLA4-Ig and dhfr gene) and a 5.0 kb of CHO genomic DNA (FIG. 7).

Based on Southern blot analysis, genomic DNA from CHO cell line P was used to clone the 7.5 and 10.0 kb flanking genomic fragments. CHO genomic DNA was isolated from $1 \times 10^8$ CHO cells grown in 200 ml of PFCHO serum free media. After centrifugation, the cell pellet was processed for isolating the genomic DNA using a DNA extraction kit (Stratagene Inc.). This procedure yielded 10 milligrams of total genomic DNA.

To enrich EcoRI digested CHO genomic DNA containing the flanking genomic sequence, one milligram of genomic DNA was digested with 1000 units of EcoRI enzyme (New England Biolabs #101S—20 units/microliter) at 37° C. for 6 hours. The EcoRI digestion was terminated by phenol extraction and ethanol precipitation. The ethanol pellet was redissolved in 200 microliters of water and was subjected to agarose bed electrophoresis in Tris-Acetate buffer at (50V) constant voltage (Life Technologies Model 250 electrophoresis unit). The size separated genomic DNA was enriched for DNA between 6.0–12.0 kb molecular weight range and extracted back from the gel using the QIAEX gel extraction kit (Qiagen Inc#20021). This procedure yielded 26 micrograms of EcoRI digested size enriched CHO DNA fragments.

One microgram of genomic DNA with the EcoRI ends was inserted into a similarly digested bacterial plasmid (pSTKN) containing kanamycin phosphotransferase gene conferring resistance to antibiotic kanamycin. The T4 DNA ligase (New England Biolabs) was used to ligate the genomic and the plasmid DNAs generating the CHO genomic library. The ligated CHO genomic DNA was transformed into *E. coli* (XL1 Blue MRF' Stratagene Inc., #200230) using electroporation equipment (Bio-Rad #) generating CHO genomic library in *E. coli*.

To clone the 7.5 kb left flanking region we took advantage of the presence of a beta lactamase gene conferring resistance to the antibiotic ampicillin. The *E. coli* cells containing the genomic library were directly screened for clones resistant to two antibiotics ($amp^R$ and $Kn^R$); the $amp^R$ was contributed by the LFR fragment and the $Kn^R$ gene was contributed by the bacterial plasmid (pSTKN). This procedure yielded eight bacterial clones resistant to both the antibiotics. Rapid DNA analysis of the plasmid DNA from these clones as expected yielded plasmids with a 7.5 kb EcoRI fragment as expected indicating the presence of the LFR fragment.

Cloning the 10.0 kb right flanking region involved conventional molecular biology techniques of colony hybridization using $P^{32}$ labeled CTLA4-Ig gene (DNA) as a hybridization probe. The colony hybridization procedure is described in the Molecular Cloning laboratory Manual (Cold Spring Laboratory). The radioactive labeled ($\alpha$-$P^{32}$ dCTP) CTLA4-Ig gene specific hybridization probe was prepared using a Nick translation kit obtained from Amersham Life Sciences (#N5000). Approximately one million *E. coli* clones were screened to isolate six putative clones containing the 10.0 kb fragment. Rescreening of the putative clones in a second round of colony hybridization generated only two positives. The plasmid DNA from two positive clones was isolated using rapid minilysate plasmid DNA isolation (as described in Maniatis, *Molecular Biology: A Laboratory Manual*, Cold Spring Harbor Laboratory, N.Y. (1989)). Both the clones generated the expected 10.0 kb EcoRI fragment, indicating the successful cloning of RFR fragment.

Figure 2:
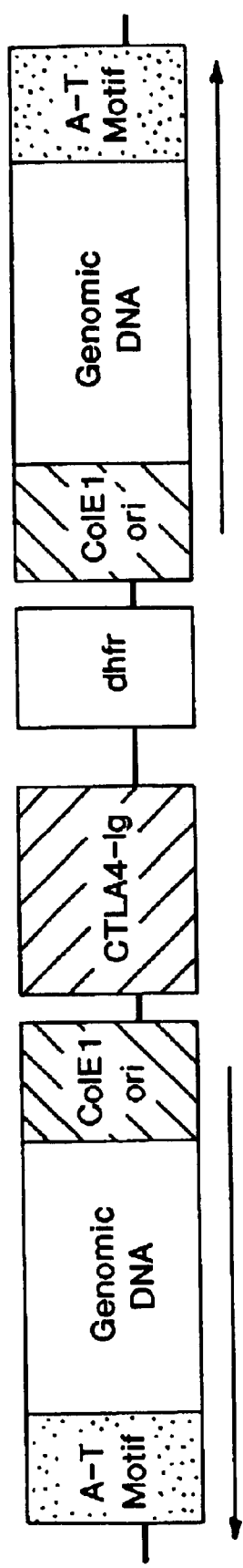
FIG. 2 represents the molecular organization of the CTLA4-Ig integration site in cell line P. It shows an identical 5.0 kb genomic sequence that flanks both ends of the CTLA4-Ig gene; an A-T rich motif; MAR's like sequence (Matrix associated regions); and Alu like sequence.

A comparison of a restriction enzyme digestion pattern of the 7.5 kb and 10.0 kb genomic clones revealed common size DNA bands invoking duplication of the genomic DNA at the site of plasmid integration. This was confirmed by DNA sequence analysis using automated DNA sequencer (Applied Biosystems—PRISM 310 Genetic Analyzer). These two results suggested that the left and right flanking sequences are identical and arose by DNA duplication at the site of integration (FIG. 2). These sequences are herein referred to as FGSs (Flanking Genomic Sequences).

DNA sequence analysis of the 5.0 kb genomic DNA revealed several unique features. A DNA homology search with the GCG Wisconsin DNA sequence data analysis software suggested that the sequence represents a transcriptional hot spot. The cloned FGS contains a DNA motif similar to a consensus Autonomous Replication Sequence (ARS) found in yeast and CHO cells. (Sohn et.al., (1996) *Journal of Bacteriology* 78(15):4420; Mark et.al., (1990) *J. Mol. Biol.* 211:19). Also, the FGSs contain motifs similar to MARs commonly found in transcriptional hot spots. (Harmutt et.al.,(1995) *Biochemistry* 34:4108). With this information that the cloned DNA is a transcriptional hot spot from CHO cells, we proceeded to construct homologous recombination vectors.

Integration of exogenous DNA into mammalian genome is thought to occur most often by a process associated with DNA breakage at random sites in the target genome. Recently, models for endogenous gene amplification as well as the amplification of heterologous transfected DNA were proposed. A component of these models is the involvement of large inverted duplication at the site of integration as a first step in the gene amplification (Heartlein M. W., et. al., (1988) *Nucleic Acid Research* 17(4):1697–1716; Passananti C., et. al., (1987) *EMBO J.* 6:1697–1703). An essential component of this model is the integration of the plasmid DNA into an A-T rich repetitive element in the host genome as a prerequisite for the formation of inverted repeat and subsequent gene amplification.

The presence of inverted duplication at the site of CTLA4-Ig integration in cell line P, and the presence of three distinct repetitive elements in the HIRPE sequence, are in agreement with the proposed model. The presence of repetitive elements in HIRPE in a homologous insertional recombination vector might facilitate the formation of inverted repeat and the gene amplification required for high expression.

EXAMPLE 2

Recombination Vectors

Homologous recombination is considered a powerful tool for genetic manipulation in yeast allowing precisely site specific gene integration and expression of the gene of intrest (Orr-Weaver, T. L., et al., (1981) *Proc. Natl. Acad. Sci. U.S.A.* 78(10):6354–8). However, potential application of homologous recombination technology in mammalian cultured cells is overwhelmed by the illegitimate recombination events and the lack of appropriate selection techniques. Homologous insertion of a recombinant gene to a hot spot permits one to study the increased frequency of high recombinant protein expressing cell lines. This concept has been described in a previous publication as one example of how to generate a homologous recombination antibody expression system for murine cells. (Gregory et.al., WO 95/17516).

Nevertheless, the present invention differs from what is known in the art in its wider applicability to all recombinant genes, the choice of the CHO genomic locus, the ability to consistently amplify the cloned recombinant genes and in generating a genomic duplication at the site of plasmid integration.

As described above, homologous recombination vectors are eukaryotic expression vectors that contain necessary elements for transcription and translation of genes to proteins. The homologous recombination vectors described herein are re-engineered vectors derived from the vector pcDNA3 (Invitrogen Inc.) containing the DHFR gene as the dominant selection marker. This expression vector may be introduced into CHO host cells DG44 and DUKXB11 cells deficient in dihydrofolate reductase enzyme, and transfectomas are selected against the background by complementing the DHFR gene function (Methotrexate metabolism in mutant Chinese hamster ovary cells lacking dihydrofolate reductase (Joannon P., et.al., (1987) *Biochem-Pharmacol.* 36(7):1091; Urlaub et.al., (1980) *Proc. natl. Acad. Sci. USA* 77:4216).

Figure 3:
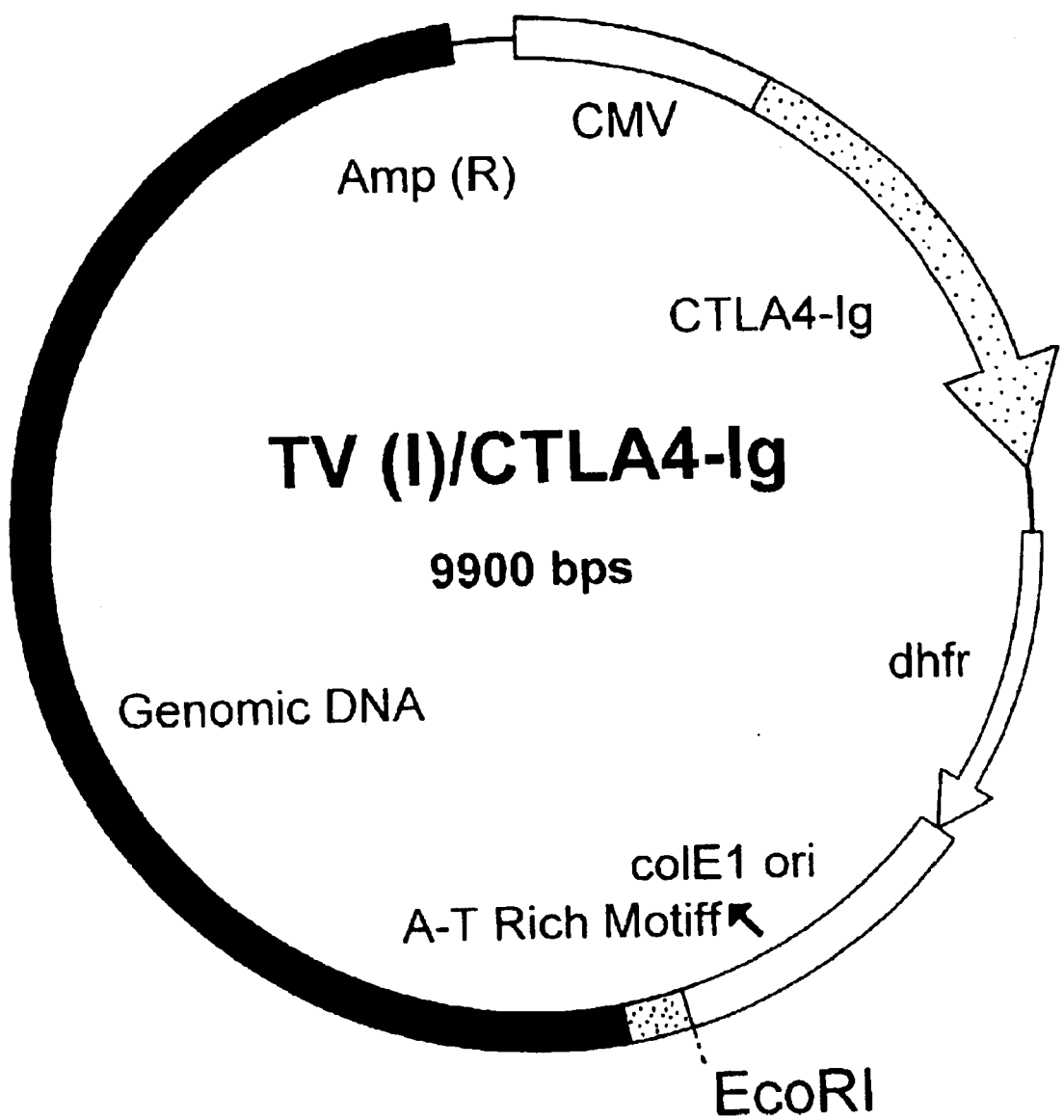
FIG. 3 shows a schematic diagram of the homologous insertional recombination vector, pTV(I).

The homologous insertional recombination vector, labeled pTV(I), contained the entire 5.0 kb HIRPE sequence (SEQ ID NO: 1) cloned genomic DNA (FIG. 3). This genomic fragment was reconstructed with a Not I restriction site at the 5' end and flush 3'(blunt) end and cloned into a pcDNA/DHFR/CTLA4-Ig expression vector that was previously digested with compatible restriction sites. The resulting homologous vector pTV(I) contained the CHO genomic DNA at the 5' end of the CTLA4-Ig recombinant gene (FIG. 3). The plasmid DNA was purified using the Midi-Plasmid Isolation Kit commercially available through QUIAGEN Inc. The pTV(I) plasmid was linearized with EcoR I restriction enzyme and electroporated into CHO DG44 cells.

After a brief recovery period (72 hours) in PFCHO media (JRH Biosciences, Serum free-protein free #14602-79P) containing nucleosides (hypoxanthine 16 $\mu$g/ml and thymidine 0.2 $\mu$g/ml), the cells were subjected to selection in PFCHO media without nucleosides and a medium containing 5% dialyzed fetal calf serum with 20 nM methotrexate. The cells were distributed into ten 96 well plates (960 wells). After a three-week incubation period, approximately 120 transfectomas were positive for CTLA4-Ig expression in an ELISA. Six clones (5%) generated the primary CTLA4-Ig protein titers greater than five micrograms/ml (Table I). The best six clones were expanded into T-75 tissue culture flasks and CHO genomic DNA was prepared for Southern blot analysis using a genomic DNA isolation kit available from Stratagene Inc.

Conventional expression vectors (e.g., pcDNA3/Neo$^R$ and pcDNA/dhfr) yielded transfectomas with the highest CTLA4-Ig protein titers of 5 micrograms/ml ($\mu$g/ml). Transfectomas that produced greater than 5 $\mu$g/ml were chosen as successfully incorporating the HIRPE sequence and exhibiting increased expression. Since 5 $\mu$g/ml is the best protein titer one can obtain with a conventional expression vector, any transfectoma expressing greater than 5 $\mu$g/ml of a desired protein, e.g., CTLA4-Ig protein, in primary titers is considered significant and an "increase" in expression.

TABLE I

| Clone # | Site Specific Integration | Primary CTLA4-Ig protein titers (micrograms/ml |
|---|---|---|
| pTV(I)-IAI | Yes | 19.9 |
| pTV(I)-3C2 | Yes | 6.2 |
| pTV(I)-3C11 | No | 8.0 |
| pTV(I)-6B8 | Yes | 9.5 |
| pTV(I)-2C5 | ND | 5.2 |
| pTV(I)-2F2 | ND | 5.1 |
| Control (pcDNA/dhfr) | ND | 1.2 |

The six clones in Table I above represent the best CTLA4-Ig producing transfectomas generated using an insertional targeting vector pTV(I). All the six clones listed in Table I contain the 5.0 kb genomic DNA. The four clones in bold letters indicate that the genomic DNA from these clones were analyzed by Southern blots. The clones 2C5 and 2F2 clones (not bold) were not analyzed by Southern blots. ND indicates "Not Determined", and was used to indicate clones that were not analyzed by Southern blots.

In our control transfections using (pcDNA/dhfr) we did not find any transfectomas expressing CTLA4-Ig titers of 5 $\mu$g/ml or greater. Conventional random integration vectors in our hands produced 1/1000 transfectomas expressing the desired protein, that is CTLA4-Ig, in titers of 5 $\mu$g/ml; based on this number, one can predict that the frequency of high producers using random integration vectors is around 1/1000 (0.1%). The data presented herein shows that homologous recombination vectors comprising the HIRPE of the present invention, compared to conventional control vectors, increases the frequency of obtaining transfectomas with high recombinant protein titers from 0.1% (controls) to 5%. This represents a fifty fold increase in the frequency of obtaining a high producer over random integration vectors.

Southern blot analysis was used to investigate the pTV(I) plasmid integration site in four independent transfectomas. The genomic DNA from the transfectomas was analyzed for the following: (a) similar DNA band pattern between clones suggesting site specific targeting; and (b) the presence of three band pattern as evidence for the formation of inverted repeat at the site of integration. Genomic DNA was prepared from four different trnasfectomas using the Genomic DNA Isolation Kit from Stratagene, Inc. Approximately ten micrograms of CHO genomic DNA was digested with Kpn I restriction enzyme for 12 hours at 37° C. The Kpn I digested genomic DNA was separated by 0.7% agarose bed gel electrophoresis at 15V for 16 hours. The gel embedded genomic DNA was denatured with 0.4M NaOH and blotted on a 0.45 micron nitrocellulose filter using Bio-Rad vacuum blotter.

Figure 5:
FIG. 5 shows a Southern blot analysis that confirms site specific integration in transfectomas containing the insertional recombination vector, pTV(I).

PCR amplification was used to generate two hybridization probes of 200 bp and 500 bp, respectively, from different regions of the 5.0 kb genomic DNA. The 200 bp hybridization probe was generated using PCR primers CTAGC-CTGCCTCACAAGCTTG (SEQ ID NO: 6) and GAGT-CAGCCTGAGATACATAG (SEQ ID NO: 7). Similarly, the 500 bp hybridization probe was generated using PCR primers GCATTTCAGCATGGTTGGCTAGC (SEQ ID NO: 8) and GGACTTCATGTCTTCTCTCCTGC (SEQ ID NO: 9). As described above in Example 1, the hybridization probes contain digoxigenin labeled UTP (Boehringer Mannheim) and they are detected by chemiluminescent detection kit (Boehringer Mannheim). The two hybridization probes were mixed in equal volumes and hybridized to nitrocellulose using similar hybridization conditions previously described (Example 1). Southern blot analysis of the parent P cell line genomic DNA digested with EcoRI and hybridized with the mixed hybridization probes (200 bp and 500 bp) generated three EcoRI DNA bands. These results suggest that two of the EcoRI bands are the result of the formation of inverted repeat at the site of integration and the third band is the undisturbed genomic homologue. Those skilled in the art can use the three DNA band pattern as a reference marker to analyze other transfectomas generated using the same expession vector for evidence of site specific integration Southern blot analysis of the genomic DNA from the top four producers containing the pTV(I) vector (IA1, 3C2, 3C11 and 6B8) digested with EcoRI generated a three-band pattern that is common to three of the four clones analyzed. The presence of three band pattern in the new transfectomas is consistent with the formation of an inverted repeat at the site of plasmid integration. Secondly, the presence of identical sized three band pattern in these transfectomas suggest that homologous recombination vectors independently targeted to an identical site in the CHO genome, generating high recombinant gene expression (FIG. 5). The Southern blot analysis further suggests that the 5.0 kb HIRPE contains motifs that induce the formation of inverted repeats and gene amplification leading to high expression Random plasmid integration is the preferred mode of integration in CHO cells (>99%). Homologous recombination events in CHO cells account for less than 0.1–0.3%. (Thomas et.al., (1987) Proc. Natl. Acad. Sci. USA 76:615). The random integration events generally do not require extensive DNA and could potentially use the entire plasmid DNA (including the 5.0 kb genomic DNA) as a substrate. If such an event occurs, the expression vector pTV(I) may integrate at a site different from the homologous site. In the present application, Southern blot analysis suggests that Applicants novel vector, against overwhelming odds, integrates in a majority of high producing clones to a single genomic locus in CHO cells.

To independently confirm that the pTV(I) plasmid consistently generates CHO transfectomas with high recombinant protein titers, a second transfection of pTV(I) plasmid into the CHO DG44 cell line was performed. The results from the second transfection are presented in Table II below. The results from the second transfection confirm that the pTV(I) vector consistently generates transfectomas with high recombinant protein titers via integraion in a preferred locus. The clones in bold letters in Table II indicate that they were subsequently analyzed by Southern blots to demonstrate site specific integration. "ND" indicates not studied.

TABLE II

| Clone | Site Specific Integration | Primary CTLA4-Ig protein titers (micrograms/ml) |
|---|---|---|
| J1 | Yes | 12.8 |
| J2 | Yes | 13.3 |
| J3 | No | 12.7 |
| J6 | Yes | 15.6 |
| control | ND | 1.2 |

While sequencing the 5.0 kb genomic DNA, we encountered an A-T rich motif that was 70% A-T rich, which failed to amplify in a PCR reaction using digeoxigenin labeled dTTP (deoxy nucleoside triphosphate) possibly due to steric hindrance. Coincidentally, highly expressed genes in mammalian genomes contain cis acting elements that are predominantly A-T rich (Mehta (1996) J. Biol. Chem. 271(52):33616). This led to the evaluation of the A-T rich motif in the 5.0 kb CHO genomic DNA as a cis acting element, augmenting recombinant gene expression downstream. We constructed two isogenic insertional vectors pTV(I)/1.6, also referred to herein as pTV(5), (comprising nucleotides 3050 through 4676 of SEQ ID NO: 1) and pTV(I)/1.4 (comprising nucleotides 3050 through 4485 of SEQ ID NO: 1) using PCR amplification and cloning of the desired product into the vector containing the CTLA4-Ig gene as the test gene (desired protein) and the DHFR gene as the positive selection marker. As described herein, the pTV(I)/1.4 vector comprising 1435 nucleotides from the 5.0 kb genomic DNA was generated using PCR primers AGCCTATCTCCAT-TCGTCA (SEQ ID NO: 10) and CCGCCGAATTCAT-GTCTGTGTTCCTGTTAGTG (SEQ ID NO: 11). The pTV (I)/1.6 vector (comprising 1626 nucleotides from the 5.0 kb genomic DNA) was generated in PCR reaction with the PCR primers: AGCCTATCTCCATTCGTCA (SEQ ID NO: 12) and CCGCCGAATTCAACCACATGGTGGCTCACAA (SEQ ID NO: 13). The PCR derived fragments were cloned into the same expression vector described above containing the CTLA4-Ig reporter gene and dhfr selection marker. These two new vectors have the same 5' end as they are generated by the common forward primer while the 3' end of the 1.4 kb HIRPE is approximately 200 bp shorter than the 1.6 kb HIRPE. Upon transformation into the CHO DG44 cells, both vectors generated approximately 120 transfectomas that were positive for CTLA4-Ig protein expression in an ELISA. (Symington et.al., (1993) J. Immunol. 150(4):1286). However, when CTLA4-Ig titers from the four top producing clones in each class were compared, the transfectomas containing the pTV(I)/1.6 (pTV(5)) vector expressed approximately four fold higher CTLA4-Ig protein titers, while the transfectomas containing pTV(I)/1.4 did not significantly improve the CTLA4-Ig protein expression. (See FIG. 8). From these results it was concluded that the 200 bp A-T rich motif in the 5.0 kb genomic DNA acts as a cis acting element augmenting recombinant gene expression in CHO cells.

The following description details the advantages of homologous replacement vectors and the construction of a replacement vector pTV(R) containing the 5.0 kb genomic DNA. Homologous recombination between introduced and chromosomal DNA using replacement vectors is widely used to introduce foreign DNA into mammalian cells. There are many variables that influence homologous recombination in CHO cells including, but not limited to, genetic locus, the amount of homologous sequence, and positive selection cassette. Although the replacement vectors have a 5–10 fold lower frequency of homologous recombination, they have the advantage of stable integration of the insert (recombinant gene) while the extraneous plasmid sequences are excised during the recombination event. This contrasts with the insertional vector (pTV(I)) where the entire plasmid sequence is inserted. In addition, replacement vectors are preferred because of the generally accepted enrichment procedures for site specific integration applicable to the replacement vector (Hasty et.al., (1991) *Mol. Cell. Bio.* 11:4509). Finally, the replacement vector in conjunction with the HSV-tk gene provides the most common enrichment procedure used for isolating transfectomas resulting from homologous recombination (Zheing et.al., (1990) *Nature* 344:170).

The nucleoside analogue acyclovir selectively kills mammalian cells expressing the HSV-thymidine kinase ("HSV-tk") gene. The HSV-tk converts acyclovir to a phosphorylated form that is toxic to the cell. As a result, only those cells expressing HSV-tk are killed and not the normal CHO cells. The HSV-tk gene is strategically placed in the replacement vector in a region that deletes the HSV-tk gene following homologous recombination, while all other recombination events (random integration) retain the gene. As a result, transfectomas resulting from homologous recombination events survive acyclovir selection while other classes of transfectomas are killed (Evrard et.al., (1996) *Cell. Biol. Toxicol.* 12(4–6):345).

Figure 4:
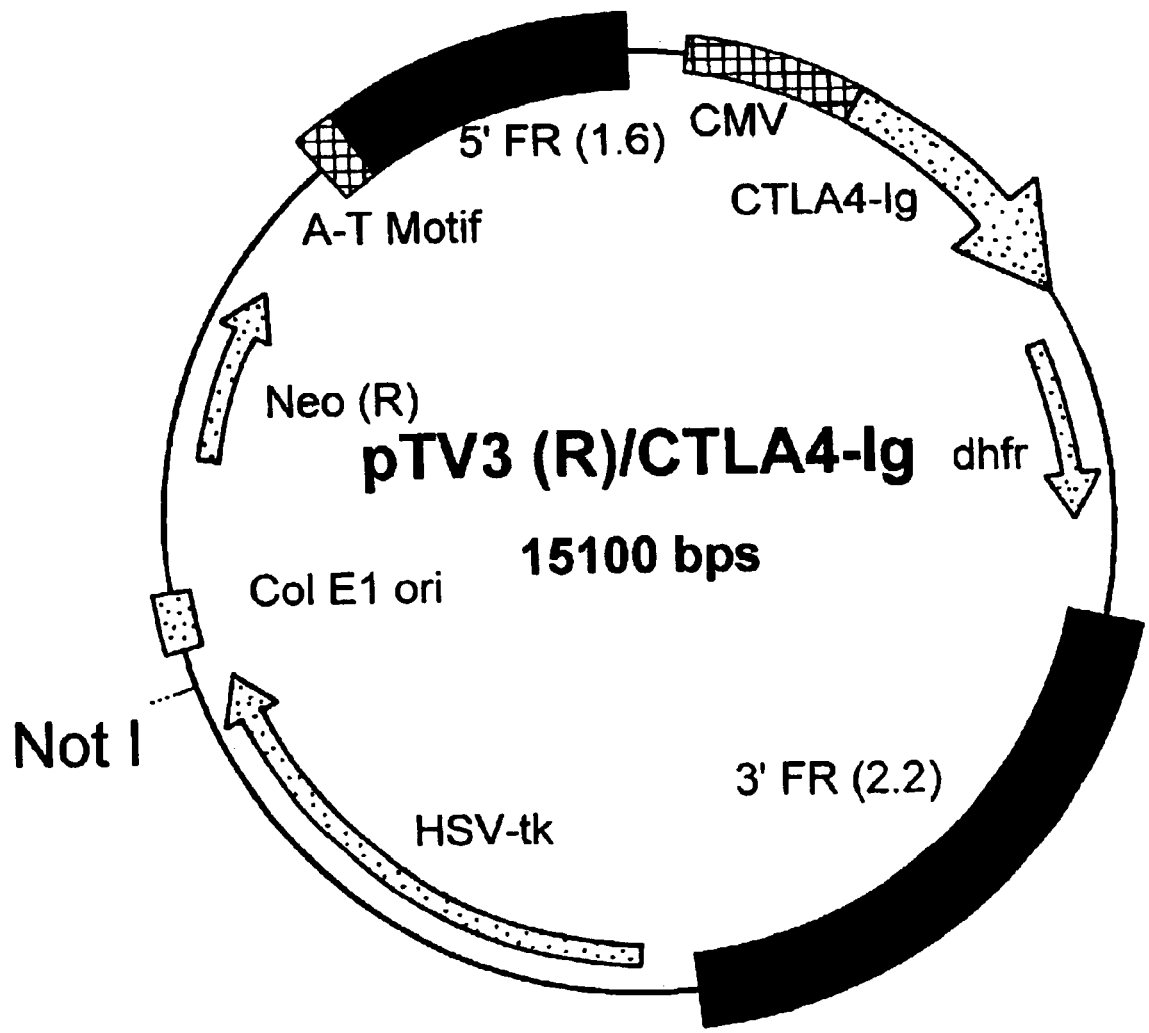
FIG. 4 shows a schematic diagram of the homologous replacement recombination vector, pTV(R).

The pTV(R) vector contains a 1.6 kb genomic DNA containing the A-T rich region at the 5' end of the CTLA4-Ig expression cassette and the 2.2 kb flanking genomic fragment at the 3' end of the DHFR selection marker (FIG. 4). The cloning of the genomic DNA into two parts is accomplished by engineering new restriction sites using polymerase chain reaction, a method readily apparent to those skilled in the art of recombinant DNA technology. The replacement vector is designed to segregate the HSV-tk gene in transfectomas resulting from homologous recombination while the illegitimate recombinants maintain the active HSV-tk gene. As a result, all illegitimate recombinants containing the active HSV-tk gene are selectively killed by the inhibitor acyclovir, and selectively allow the clones resulting from a site specific recombination to grow (Pfizer et.al., (1987) *Am. J. Cancer* 40:114; Davidson et.al., (1981) *Virology* 113:9).

The strategy of the selective enrichment of site specific recombinants yielded results as expected, and 10% of all the transfectomas generated using the replacement vector survived the selection. Electroporation of pTV(R) into the CHO cell line DG44 generated 860 transfectomas that survived the first round of 20 nM methotrexate selection. However, after the second selection with 1.0 mM acyclovir, only 94 transfectomas (10%) survived. The transfectomas surviving the double selection are due to site specific recombination events. All the 94 transfectomas were screened for CTLA4-Ig protein titers. The top six transfectomas with the highest CTLA4-Ig protein titers are presented in Table III below.

TABLE III

| Clone # | Site Specific Integration | CTLA4-Ig protein titer (micrograms/ml) |
|---|---|---|
| IC9 | Yes | 19.6 |
| 2B11 | Yes | 13.8 |
| 3D5 | Yes | 14.4 |
| 4F4 | Yes | 11.2 |
| 5C4 | Yes | 11.8 |

TABLE III-continued

| Clone # | Site Specific Integration | CTLA4-Ig protein titer (micrograms/ml) |
|---|---|---|
| 6F1 | Yes | 12.4 |
| Control | ND | 1.2 |

Figure 6:
FIG. 6 shows a Southern blot analysis that confirms site specific targeting in transfectomas containing the replacement recombination vector, pTV(R). The blot reveals a 3.5 kb band in all 5 clones suggesting that the replacement vector targets to a similar genomic locus.

The genomic DNA from the six transfectomas (i.e., IC9, 2B11, 3D5, 4F4, 5C4, and 6F1) was prepared using the procedures described above. The genomic DNA was digested with Bsp 1201 restriction enzyme and subjected to Southern blot analysis using the 200 bp and 500 bp PCR generated hybridization probes are described in the previous section. The agarose gel bed electrophoresis and hybridization conditions including the washing conditions were identical to the conditions described earlier. The DNA band pattern from all the six clones analyzed revealed an identical two band pattern with 3.5 kb and 2.7 kb bands, respectively (FIG. 6). It was inferred from these results that the 2.7 kb DNA band represents the undisrupted genomic homologue and the 3.5 kb DNA is a hybrid band containing the plasmid and genomic DNA representing integration site in the CHO genome. The presence of a common 3.5 kb hybrid fragment from all six transfectomas analyzed indicates that homologous replacement vectors are selectively integrated in a specific site in CHO genome. Furthermore, protein production remained high after reducing the number of transfectomas generated using the HSV-tk gene in the replacement vectors comprising the HIRPE gene of the present invention (SEQ ID NO: 1), or a fragment thereof (SEQ ID NO: 2).

EXAMPLE 3

Cloning and Expression of LEA29Y-Ig in Homologous Recombination Vector PTV(I)

DNA encoding LEA29Y-Ig was inserted into the homologous recombination vector pTV(I) cut with Mlu 1 and Xho I (converted to a blunt end with T4 DNA polymerase). The ligation mixture containing the pTV(I)/LEA29Y-Ig was electroporated into *E. coli* (XLI Blue, Stratagene) and single colonies containing the correct hybrid plasmid were screened using DNA mini-lysate analysis. Two independent bacterial clones with the expected plasmid were identified and the plasmid DNA was amplified using a Midi-plasmid purification kit (Stratagene).

Ten micrograms of plasmid DNA (pTV(I)/LEA29Y-Ig) were linearized with restriction enzyme EcoRI and the DNA was electroporated into CHO cell line DG44. Several CHO transfectomas containing the pTV(I) plasmid were identified approximately 21 days after electropoartion. The growth media from these transfectomas were analyzed for secreted LEA29Y-Ig protein using ELISA. Several CHO transfectomas expressing LEA29Y-Ig protein between 2.5 to 3.5 micrograms/ml were identified and picked for scale up growth study.

EXAMPLE 4

Antibody Expression Using pTV(I) Expression Vector

CHO transfectomas expressing antibodies were generated using the homologous recombination vector pTV(I) and a co-transfection strategy. In this procedure the light chain and heavy chain genes are cloned into separate vectors such as pTV(1)(LC) and pTV(I)(HC) which are mixed prior to electroporation. Typically 25% of all the tranfectomas generated using the co-transfection strategy contain both heavy and light gene expressing from the same cell, producing functional antibody.

To establish the proof of principle, we separately cloned the anti-CD40 antibody heavy chain genes into pTV(I) vector and anti-CD40 light chain gene into pTV(5) vector. Both the plasmids pTV(I)/ HC and pTV(5)/LC were cut with Mlu I to linearize the vector before transfection, mixed together in equal concentration and co-transfected into CHO cells by electroporation. These co-tranfection studies yielded several CHO tranfectomas expressing functional antibodies as analyzed by ELISA.

The above disclosure demonstrates that the present invention provides a unique and reliable way to increase expression of recombinant proteins. Using the HIRPE sequence (SEQ ID NO: 1) taught by the inventors, or a fragment of SEQ ID NO: 1 that exhibits HIRPE activity (preferably the fragment as shown in SEQ ID NO: 2), one skilled in the art can not only increase the percentage of cells that are successfully transfected, but also increase the expression in those transfected cells.

Although the present invention has been described in some detail by way of illustration and example for purposes of clarity and understanding, it will be apparent that certain changes and modifications may be practiced within the scope of the appended claims.

We claim:

1. An expression vector comprising an isolated nucleic acid sequence comprising: (a) the sequence as shown in SEQ ID NO: 1; (b) the complement of (a); or (c) a fragment of SEQ ID NO:1, wherein said nucleic acid sequence is capable of increasing the expression of a CTLA4 variant.

2. The expression vector of claim 1 further comprising a selectable marker.

3. The expression vector of claim 1 comprising nucleotides 3059 through 4709 of SEQ ID NO:1.

4. The expression vector of claim 1 wherein the CTLA4 variant is LEA29YIg.

5. The expression vector of claim 1, further comprising a nucleic acid sequence encoding LEA29YIg.

6. The expression vector of claim 3, further comprising a nucleic acid sequence encoding LEA29YIg.

7. A host cell transformed with the expression vector of claim 1.

8. A host cell transformed with the expression vector of claim 2.

9. A host cell transformed with the expression vector of claim 3.

10. A host cell transformed with the expression vector of claim 5.

11. A CHO cell transformed with the expression vector of claim 1.

12. A CHO cell transformed with the expression vector of claim 2.

13. A CHO cell transformed with the expression vector of claim 3.

14. A CHO cell transformed with the expression vector of claim 5.

15. An expression vector comprising an isolated nucleic acid sequence comprising: (a) the sequence as shown in SEQ ID NO: 1; (b) the complement of (a); or (c) a fragment of SEQ ID NO:1 wherein said nucleic acid sequence is capable of increasing the expression of a recombinant protein of interest wherein said recombinant protein of interest is an antibody.

16. An expression vector of claim 15 further comprising two nucleic acid sequences encoding different polypeptides in the same vector which assemble into a protein of interest with biological activity.

17. A host cell transformed with two expression vectors wherein each of the expression vectors comprises an isolated nucleic acid sequence capable of increasing the expression of a recombinant protein of interest said nucleic acid sequence comprising: (a) the sequence as shown in SEQ ID NO:1; (b) the complement of (a); or (c) a fragment of SEQ ID NO:1, and wherein each of the two expression vectors encodes a polypeptide subunit that when coexpressed in the host cell assembles into a protein of interest with biological activity.

18. The host cell of claim 17 wherein the protein of interest is anti-CD40 antibody.

19. A method for obtaining a recombinant LEA29YIg, comprising culturing a host cell according to claim 10 under conditions promoting expression of said LEA29YIg and recovering the LEA29YIg.

20. A method for obtaining a recombinant biologically active anti-CD40 antibody, comprising culturing a host cell according to claim 24 under conditions promoting expression of said anti-CD40 antibody, and recovering the anti-CD40antibody.

21. The expression vector of claim 1, wherein the CTLA4 variant is L104EIg.

22. The expression vector of claim 1, further comprising a nucleic acid sequence encoding L104EIg.

23. The expression vector of claim 2 wherein the CTLA4 variant is selected from the group consisting of LEA29YIg and L104EIg.

24. The expression vector of claim 3, further comprising a nucleic acid sequence encoding L104EIg.

25. A host cell transformed with the expression vector of claim 22.

26. A host cell transformed with the expression vector of claim 24.

27. A method for obtaining a recombinant L104EIg, comprising culturing a host cell according to claim 25 under conditions promoting expression of said L104EIg and recovering the L104EIg.

* * * * *